US006998116B1

(12) United States Patent
Ashkenazi

(10) Patent No.: US 6,998,116 B1
(45) Date of Patent: Feb. 14, 2006

(54) APO-2 LIGAND

(75) Inventor: Avi J. Ashkenazi, San Mateo, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 09/459,808

(22) Filed: Dec. 13, 1999

Related U.S. Application Data

(63) Continuation of application No. 08/584,031, filed on Jan. 9, 1996, now Pat. No. 6,030,945.

(51) Int. Cl.
A61K 38/19 (2006.01)
C07K 14/52 (2006.01)

(52) U.S. Cl. .................. 424/85.1; 530/350; 530/402; 930/140; 514/12

(58) Field of Classification Search .............. 514/12, 514/43; 530/350, 402; 435/69.1, 252.33; 930/140; 424/85.1
See application file for complete search history.

(56) References Cited

U.S. PATENT DOCUMENTS

| | | | |
|---|---|---|---|
| 3,691,016 A | 9/1972 | Patel | |
| 3,969,287 A | 7/1976 | Jaworek et al. | |
| 4,179,337 A * | 12/1979 | Davis et al. ............... | 424/94.3 |
| 4,195,128 A | 3/1980 | Hildebrand et al. | |
| 4,206,226 A | 6/1980 | Gale et al. | |
| 4,229,537 A | 10/1980 | Hodgins et al. | |
| 4,247,642 A | 1/1981 | Hirohara et al. | |
| 4,301,144 A | 11/1981 | Iwashita et al. | |
| 4,330,440 A | 5/1982 | Ayers et al. | |
| 4,342,566 A | 8/1982 | Theofilopoulos et al. | |
| 4,399,216 A | 8/1983 | Axel et al. | |
| 4,419,446 A | 12/1983 | Howley et al. | |
| 4,496,689 A | 1/1985 | Mitra | |
| 4,601,978 A | 7/1986 | Karin | |
| 4,640,835 A | 2/1987 | Shimizu et al. | |
| 4,670,417 A | 6/1987 | Iwasaki et al. | |
| 4,676,980 A | 6/1987 | Segal et al. | |
| 4,791,192 A | 12/1988 | Nakagawa et al. | |
| 4,816,567 A | 3/1989 | Cabilly et al. | |
| 4,965,199 A | 10/1990 | Capon et al. | |
| 5,010,182 A | 4/1991 | Brake et al. | |
| 5,149,319 A * | 9/1992 | Unger ......................... | 424/450 |
| 5,364,934 A | 11/1994 | Drayna et al. | |
| 5,457,187 A * | 10/1995 | Gmeiner et al. ............ | 536/25.5 |
| 5,484,399 A * | 1/1996 | DiResta et al. ............. | 600/561 |
| 5,688,773 A * | 11/1997 | Chiocca et al. ............ | 424/93.1 |
| 5,763,223 A | 6/1998 | Wiley et al. | |
| 5,773,476 A * | 6/1998 | Chen et al. ................. | 514/618 |
| 2002/0115613 A1 | 8/2002 | Kumar | |

FOREIGN PATENT DOCUMENTS

| | | |
|---|---|---|
| DE | 266710 | 4/1989 |
| EP | 003089 | 7/1979 |
| EP | 036776 | 9/1981 |
| EP | 073657 | 3/1983 |
| EP | 117058 | 8/1984 |
| EP | 117060 | 8/1984 |
| EP | 304247 | 3/1989 |
| EP | 321196 | 6/1989 |
| EP | 362179 | 4/1990 |
| EP | 417563 | 3/1991 |
| GB | 2211504 | 7/1989 |
| WO | WO 87/05330 | 9/1987 |
| WO | WO 89/05859 | 6/1989 |
| WO | WO 90/13646 | 11/1990 |
| WO | WO 91/00358 | 1/1991 |
| WO | WO 91/00360 | 1/1991 |
| WO | WO 91/08291 | 6/1991 |
| WO | WO 92/20373 | 11/1992 |
| WO | WO 93/08829 | 5/1993 |
| WO | WO 94/04679 | 3/1994 |
| WO | WO 94/04690 | 3/1994 |
| WO | WO 94/29348 | 12/1994 |
| WO | WO 95/10540 | 4/1995 |
| WO | WO 95/11301 | 4/1995 |
| WO | WO 95/31544 | 11/1995 |
| WO | WO 97/01633 | 1/1997 |
| WO | WO 97/25428 | 7/1997 |
| WO | WO 97/33899 | 8/1997 |
| WO | WO 97/46686 | 12/1997 |
| WO | WO 02/053727 | 7/2002 |
| WO | WO 02/069995 | 9/2002 |

OTHER PUBLICATIONS

Weller et al. CD95 ligand: lethal weapon against malignant glioma?. Brain Pathology, (Apr. 1998) 8 (2) 285-93.*

Lutz et al. MycN and IFNgamma cooperate in apoptosis of human neuroblastoma cells. Oncogene, (Jul. 23, 1998) 17 (3) 339-46.*

Rieger et al. APO2 ligand: a novel lethal weapon against malignant glioma? FEBS Letters, (May 1, 1998) 427 (1) 124-8.*

Alberts et al., Molecular Biology of the Cell, Jan. 1983, Garland Publishing, Inc., New York, NY, page(s) 264-266.*

Alberts et al. Molecular Biology of the Cell, 3rd edition, New York:Garland Publishing, Inc. pps. 415-416 (1994).

Alberts et al., "Molecular Biology of the Cell", ., New York, NY:Garland Publishing, Inc. pps. 1267 (Jan. 1994).

Amakawa et al., "The Hodgkin Disease Antigen CD30 is Crucial for Antigen-induced Death of Developing T Cells" Cold Spring Harbor Laboratory Symposium on Programmed Cell Death (Abstr. No. 10) (1995).

(Continued)

Primary Examiner—David S. Romeo
(74) Attorney, Agent, or Firm—Diane L. Marschang

(57) ABSTRACT

A novel cytokine, designated Apo-2 ligand, which induces mammalian cell apoptosis is provided. The Apo-2 ligand is believed to be a member of the TNF cytokine family. Compositions including Apo-2 ligand chimeras, nucleic acid encoding Apo-2 ligand, and antibodies to Apo-2 ligand are also provided. Methods of using Apo-2 ligand to induce apoptosis and to treat pathological conditions such as cancer, are further provided.

8 Claims, 8 Drawing Sheets

OTHER PUBLICATIONS

Aplin et al., "Preparation, Properties, and Applications of Carbohydrate Conjugates of Proteins and Lipids" *CRC Crit. Rev. Biochem.* 10(4) :259-306 (1981).

Ashkenazi and Chamow, "Immunoadhesins: An Alternative to Human Monoclonal Antibodies" *Methods: A Companion to Methods in Enzymology* 8:104-115 (1995).

Ashkenazi et al., "Induction of Apoptosis by APO-2 Ligand, a New member of the Tumor Necrosis Factor Cytokine Family" *European Cytokine Network* 7:159 (1996).

*Antologous Bone Marrrow Transplantation: Proceedings of the Third International Symposium*, Dicke et al., University of Texas M.D. Anderson Hospital (1987).

Banerji et al., "A Lymphocyte-specific Cellular Enhancer Is Located Downstream of the Joining Region in Immunoglobulin Heavy Chain Genes" *Cell* 33:729-740 (Jul. 1983).

Barr et al., "Apoposis and Its Role in Human Disease" *Bio/Technology* 12:487-493 (1994).

Bianchi et al., "Transformation of the yeast *Kluyveromyces lactis* by New Vectors Derived from the 1.6 $\mu$m Circular Plasmid pkD1" *Curr. Genet.* 12:185-192 (1987).

"BLAST Results A-1-A-36" (Genbank).

"BLAST Results B-1-B-25" (Dayhoff).

Boerner et al., "Production of Antigen-Specific Human Monoclonal Antibodies From In Vitro-Primed Human Splenocytes" *The Journal of Immunology* 147(1):86-95 (1991).

Bowie et al., "Deciphering the Message in Protein Sequences: Tolorence to Amino Acid Substitutions" *Science* 247:1306-1310 (1990).

Brockhaus et al., "Identification of two types of tumor necrosis factor receptors on human cell lines by monoclonal antibodies" *Proc. Natl. Acad. Sci. USA* 87:3127-3131 (1990).

Brodeur et al., "Mouse-Human Myeloma Partners for the Production of Heterohybridomas" *Monoclonal Antibody Production Techniques and Applications*, New York:Marcel Dekker, Inc. pps. 51-63 (1987).

Browning et al., "Lymphotoxin $\beta$, a Novel Member of the TNF Family That Forms a Heteromeric Complex with Lymphotoxin on the Cell Surface" *Cell* 72:847-856 (1993).

Bruggemann et al., "Designer Mice: The Production of Human Antibody Repertoires in Transgenic Animals" *Year in Immunology* 7:33-40 (1993).

Byrn et al., "Biological Properties of a CD4 Immunoadhesin" *Nature* 344:667-670 (Apr. 12, 1990).

Canaani et al., "Regulated Expression of Human Interferon $\beta_1$ Gene After Transduction into Cultured Mouse and Rabbit Cells" *Proc. Natl. Acad. Sci. USA* 79:5166-5170 (1982).

Carter et al., "Humanization of an anti-p185$^{HER2}$ antibody for human cancer therapy" *Proc. Natl. Acad. Sci.* 89:4285-4289 (May 1992).

Chamow et al., "A Humanized, Bispecific Immunoadhesin-Antibody that Retargets CD3$^+$ Effectors to Kill HIV-1-Infected Cells" *Journal of Immunology* 153:4268-4280 (1994).

Chang et al., "Phenotypic Expression in *E. coli* of a DNA Sequence Coding for Mouse Dihydrofolate Reductase" *Nature* 275:617-624 (Oct. 19, 1978).

*Chemotherapy Service Ed.*, M. C. Perry, Baltimore, MD: Williams & Wilkins (1992).

Chothia and Lesk, "Canonical structures for the hypervariable regions of immunoglobulins" *J. Mol. Biol.* 196(4):901-917 (1987).

Cohen, "Programmed Cell Death in the Immune System" *Advances in Immunol.* 50:55-85 (1991).

Cole et al., "The EBV-Hybridoma Technique and Its Application to Human Lung Cancer" *Monoclonal Antibodies and Cancer Therapy*, Reisfeld et al., New York:Alan R. Liss, Inc. pps. 77-96 (1985).

Creighton., "Protein Biosynthesis" *Proteins: Structures and Molecular Principles*, San Francisco:W.H. Freeman & Co. pps. 79-86 (1983).

Darzynkiewicz et al., "Assays of Cell Viability: Discrimination of Cells Dying by Apoptosis" *Methods in Cell Biol.* 41:15-38 (1994).

David et al., "Protein Iodination with Solid State Lactoperoxidase" *Biochemistry* 13(5):1014-1021 (1974)

Dealtry et al., "DNA Fragmentation and Cytotoxicity Caused by Tumor Necrosis Factor is Enhanced by Interferon-$\gamma$" *European Journal of Immunology* 17:689-693 (1987).

deBoer et al., "The TAC Promoter: A functional Hybrid Derived From the TRP and LAC Promoters" *Proc. Natl. Acad. Sci. USA* 80:21-25 (1983).

Depicker et al., "Napaline Synthase: Transcript Mapping and DNA Sequence" *J. Mol. Appl. Gen.* 1:561-573 (1982).

Dieffenbach et al., *PCR Primer: A Laboratory Manual*, Cold Spring Harbor Laboratory Press pps. 1-16;133-142 (1995).

Duksin et al., "Relationship of the Structure and Biological Activity of the Natural Homologues of Tunicamycin" *Journal of Biological Chemistry* 257:3105-3109 (1982).

Eck and Sprang, "The structure of tumor necrosis factor-$\alpha$ at 2.6 A resolution" *Journal of Biological Chemistry* 264 (29):17595-17604 (1989).

Eck et al., "The Structure of Human Lymphotoxin (Tumor Necrosis Factor-$\beta$) at 1.9-A Resolution" *J. Bio. Chem.* 267:2119-2122 (1992).

Edge et al., "Deglycosylation of glycoproteins by trifluoromethanesulfonic acid" *Analytical Biochemistry* 118: 131-137 (1981).

Evan et al., "Isolation of Monoclonal Antibodies Specific for Human c-myc Proto-Oncogene Product" *Molecular & Cellular Biology* 5:3610-3616 (1985).

Fadok et al., "Exposure of Phosphatidylserine on the Surface of Apoptotic Lymphocytes Triggers Specific Recognition and Removal by Macrophages" *J. Immunol.* 148:2207-2216 (1992).3

Field et al., "Purification of a RAS-Responsive Adenylyl Cyclase Complex from *Saccharomyces cerevisiae* by Use of an Epitope Addition Method" *Molecular & Cellular Biology* 8:2159-2165 (1988).

Fiers et al., "Complete Nucletide Sequence of SV40 DNA" *Nature* 273:113-120 (May 11, 1978).

Fleer et al., "Stable Multicopy Vectors for High-Level Secretion of Recombinant Human Serum Albumin by Kluyveromyces Yeasts" *Bio/Technology* 9:968-975 (1991).

Gething et al., "Cell-surface Expression of Influenza Haemagglutinin from a Cloned DNA Copy of the RNA Gene" *Nature* 293:620-625 (Oct. 22, 1981).

Goding, "Production of Monoclonal Antibodies" *Monoclonal Antibodies: Principles and Practice*, Academic Press, pps. 59-103 (1986).

Goedel et al., "Direct Expression in *Escherichia coli* of a DNA Sequence Coding for Human Growth Hormane" *Nature* 281:544-548 (Oct. 18, 1979).

Goeddel et al., "Synthesis of Human Fibroblast Interferon by *E. coli*" *Nucleic Acids Research* 8(18):4057-4074 (1980).

Goodwin et al., "Molecular cloning and expression of the type 1 and type 2 murine receptors for tumor necrosis factor" *Molecular & Cellular Biology* 11:3020-3026 (1991).

Gorman et al., "The Rous Sarcoma Virus Long Terminal Repeat is a Strong Promoter When Introduced into a Variety of Eukaryotic Cells by DNA-Mediated Transfection" *Proc. Natl. Acad. Sci. USA* 79:6777-6781 (Nov. 1982).

Graham et al., "A New Technique for the Assay of Infectivity of Human Adenovirus 5 DNA" *Virology* 52:456-467 (1973).

Graham et al., "Characteristics of a Human Cell Line Transformed by DNA from Human Adenovirus Type 5" *J. Gen. Virol.* 36:59-72 (1977).

Gray et al., "Expression of Human Immune Interferon cDNA in *E. coli* and Monkey Cells" *Nature* 295:503-508 (Feb. 11, 1982).

Greenway et al., "Human Cytomegalovirus DNA: BamHI, EcoRI and PstI Restriction Endouclease Cleavage Maps" *Gene* 18:355-360 ()1982).

Grell et al., "The Transmembrance Form of Tumor Necrosis Factor Is the Prime Activating Ligand of the 80 kDNA Tumor Necrosis Factor Receptor" *Cell* 83:793-802 (Jan. 1, 1995).

Gruss and Dower, "Tumor Necrosis Factor Ligand Superfamily: Involvement in the Pathology of Malignant Lymphomas" *Blood* 85:3379-3404 (1995).

Hess et al., "Cooperation of Glycolytic Enzymes" *Advances in Enzyme Regulation*, George Weber, New York:Pergamon Press vol. 7:149-167 (1968).

Hitzeman et al., "Isolation and Characterization of the Yeast 3-Phosphoglycerokinase Gene (PGK) by an Immunological Screening Technique" *Journal of Biological Chemistry* 255(24):12073-12080 (Dec. 25, 1980).

Hochuli et al., "Genetic approch to facilitate purification of recominant proteins with a novel ovel, vel manovel" *Bio-Technology* pps/ 1321-1325 (Nov. 1988).

Hohmann et al., "Two different cells types have different major receptors for human tumor necrosis factor (TNFα)" *Journal of Biological Chemistry* 264(25):14927-14934 (1989).

Holland et al., "Isolation and Identification of Yeast Messanger Ribonucleic Acids Coding for Enolase, Glyceraldehyde-3-phosphate Dehyrogenase, and Phosphoglycerate Kinase" *Biochemistry* 17(23):4900-4907 (1978).

Hoogenboom and Winter, "By-passing immunisation: human anitbodies from synthetic repertoires of germline $V_H$ gene segments rearranged in vitro" *J. Mol. Biol.* 227:381-388 (1992).

Hopp et al., " A Short Polypeptide Marker Sequence Useful for Recombinant Protein Identification and Purification" *Bio/Technology* 6:1204-1210 (1988).

Hsiao et al., "High-frequency Transformation of Yeast by Plasmids Containing the Cloned Yeast Arg4 Gene" *Proc. Natl. Acad. Sci. USA* 76:3829-3833 (1979).

Hunter et al., "Preparation of Iodine 131 Labelled Human Growth Hormane of High Specific Activity" *Nature* 194:495-496 (1962).

Itoh et al., "The polypeptide encoded by the cDNA for human cell surface antigen Fas can mediate apoptosis" *Cell* 66:233-243 (1991).

Jakobovits et al., "Analysis of Homozygous Mutant Chimeric Mice: Deletion of the Immunoglobulin Heavy-Chain Joining Region Blocks B-cell Development and Antibody Production" *Proc. Natl. Acad. Sci. USA* 90:2551-2555 (Mar. 1993).

Jakobovits et al., "Germ-line Transmission and Expression of a Human-Derived Yeast Artificial Chromosome" *Natural* 362:255-258 (Mar. 18, 1993).

Jones et al., "Replacing the Complementarity-determining Regions in a Human Antibody with Those From a Mouse" *Nature* 321:522-525 (May 29, 1986).

Jones, E., "Proteinase Mutants of *Saccharomyces cerevisiae*" *Genetics* 85(1):23-33 (1977).

Keown et al., "Methods for Introducing DNA into Mammalian Cells" *Methods in Enzymology* 185:527-537 (1990).

Kingsman et al., "Replication in *Saccharomyces cerevisiae* of Plasmid pBR313 Carrying DNA from the Yeast trpl Region" *Gene* 7:141-152 (1979).

Kohler et al., "Continuous Cultures of Fused Cells Secreting Anitbody of Predefined Specificity" *Nature* 256:495-497 (Aug. 7, 1975).

Koopman et al., "Annexin V for Flow Cytometric Detection of Phosphatidylserine Expression on B Cells Undergoing Apoptosis" *Blood* 84:1415-1420 (1994).

Kozak, "An analysis of vertebrate mRNA sequences: intimations of translational control" *Journal of Cell Biology* 115:887-903 (1991).

Kozbor et al., "A Human Hybrid Myeloma for Production of Human Monoclonal Antibodies" *The Journal of Immunology* 133(6):3001-3005 (1984).

Krammer et al., "Regulation of Apoptosis in the Immune System" *Curr. Op. Immunol.* 6:279-289 (1994).

Laimins et al., "Osmotic Control of kdp Operon Expression in *Escherichia coli*" *Proc. Natl. Acad. Sci. USA* 78(1):464-468 (Jan. 1981).

Lasky et al., "DNA sequence analysis of the type-common glycoprotein-D genes of herpes simplex virus types 1 and 2" *DNA* 3(1):23-29 (1984).

Lasky et al., "Neuralization of the AIDS Retrovirus by Antibodies to a Recombinant Envelope Glycoprotein" *Science* 233:209-212 (1986).

Lenardo, "Interluekin-2 Programs Mouse αβ T Lymphocytes for Apoptosis" *Nature* 353:858-861 (1991).

Lewis et al., "Cloning and expression of cDNAs for two distinct murine tumor necrosis factor receptors demonsrates one receptor is species specific" *Proc. Natl. Acad. Sci. USA* 88:2830-2834 (1991).

Loetscher et al., "Molecular Cloning and Expression of the Human 55 kd Tumor Necrosis Factor Receptor" *Cell* 61:351-359 (Apr. 20, 1990).

Luckow et al., "Trends in the Development of Baculovirus Expression Victors" *Bio/Technology* 6:47-55 (1988).

Lusky et al., "Bovine Papilloma Virus Contains an Activator of Gene Expression at the Distal End of the Early Transcriptional Unit" *Molecular & Cellular Biology* 3(6):1108-1122 (Jun. 1983).

Lutz-Freyermuth et al., "Quantitative Determination That One of Two Potential RNA-binding Domains of the A Protein Component of the U1 Small Nuclear Ribonucleoprotein Complex Binds with High Affinity to Stem-loop II of U1 RNA" *Proc. Natl. Acad. Sci. USA* 87:6396-6397 (1990).

Maeda et al., "Production of Human α-interferon in Silkworm Using a Baculovirus Vector" *Nature* 315:592-594 (Jun. 13, 1985).

Mage et al., "Preparation of Fab and F(ab')₂ Fragments from Monoclonal Antibodies" *Monoclonal Antibody Production Techniques and Applications*, New York:Marcel Dekker, Inc. pps. 79-97 (1987).

*Mammalian Cell Biotechnology: A Practical Approach*, M. Butler, ed., IRL Press (1991).

Mansour et al., "Distruption of the Proto-oncogene int-2 in Mouse Embryo-derived Stem Cells: a General Strategy for Targeting Mutations to Non-selectables Genes" *Nature* 336:348-352 (1988).

Mantei et al., "Rabbit β-globin mRNA Production in Mouse L Cells Transformed with Cloned Rabbit β-globin Chromosomal DNA" *Nature* 281:40-46 (Sep. 6, 1079).

Marks et al., "By-passing immunization: human antibodies from V-gene libraries displayed on phage" *J. Mol. Biol.* 222:581-597 (1991).

Martin et al., "GAP Domains Responsible for Ras p21-Dependent Inhibition of Muscarinic Atrial $K^+$ Channel Currents" *Science* 255:192-194 (1992).

Mather et al., "Culture of Testicular Cells in Hormone-Supplemented Serum-Free Medium" *Annals N.Y. Acad. Sci.* 383:44-68 (1982).3

Mather et al., "Establishment and Characterization of Two Distinct Mouse Testicular Epithelial Cell Lines" *Biol. Reprod.* 23:243-252 (1980).

Maxam et al., "Sequencing End-labeled DNA with Base-Specific Chemical Cleavages" *Methods in Enzymology* 65:499-560 (1980).

McCafferty et al., "Phage antibodies: filamentous phage displaying antibody variable domains" *Nature* 348:552-554 (1990).

Messing et al., "A System for Shotgun DNA Sequencing" *Nucleic Acids Research* 9(2):309-321 (1981).

Miller et al., "An Insect Baculovirus Host-Vector System for High-Level Expression of Foreign Genes" *Genetics Engineering*, Setlow et al., Plemum Publishing vol. 8:277-298 (1986).

Milstein et al., "Hybrid Hybridomas and Their Use in Immunohistochemistry" *Nature* 305:537-540 (1983).

Moore et al., "Apoptosis in CHO Cell Batch Cultures: Examination by Flow Cytometry" *Cytotechnology* 17:1-11 (1995).

Mordenti et al., "Interspecies Scaling of Clearance and Volume of Distribution Data for Five Therapeutic Proteins" *Pharmaceutical Research* 8(11):1351-1359 (1991).

Mulligan et al., "Expression of a Bacterial Gene in Mammalian Cells" *Science* 209:1422-1427 (Sep. 1980).

Munson et al., "LIGAND: A Versatile Computerized Approach for Characterization of Ligand-Binding Systems" *Analytical Biochemistry* 107:220-239 (1980).

Nagata et al., "The Fas Death Factor" *Science* 267:1449-1456 (1995).

Nygren, H., "Conjugation of Horseradish Peroxidase to Fab Fragments with Different Homobifunctional and Heterobifunctional Cross-Linking Reagents" *The Journal of Histochemistry and Cytochemistry* 30(5):407-412 (1982).

O'Reilley et al. *Baculovirus Expression Vectors: A Laboratory Manual*, Oxford:Oxford University Press (1994).

Osborne et al., "Transcriptional Control Region Within the Protein-coding Portion of Adenvirus E1A Genes" *Molecular & Cellular Biology* 4(7):1293-1305 (1984).

Paborksy et al., "Mammalian Cell Transient Expression of Tissue Factor for the Production of Antigen" *Protein Eng.* 3(6):547-553 (1990).

Pain et al., "Preparation of Protein A-Peroxidase Monoconjugate Using a Heterobifunctional Reagent, and its Use in Ezyme Immunoassays" *Journal of Immunological Methods* 40:219-230 (1981).

Pavlakis et al., "Expression of Two Growth Hormane Genes in Monkey Cells Infected by Simian Virus 40 Recombinants" *Proc. Natl. Acad. Sci. USA* 78(12):7398-7402 (Dec. 1981).

Pennica et al., "Expression cloning of cardiotrophin 1, a cytokine that induces cardiac myocyte hypertrophy" *Proc. Natl. Acad. Sci. USA* 92:1142-1146 (Feb. 1995).

Pitti et al., "Introduction of Apoptosis by Apo-2 Ligand, a New Member of the Tumor Necrosis Factor Cytokine Family" *Journal of Biological Chemistry* 271:12687-12690 (1996).

Presta et al., "Humanization of an Antibody Directed Against IgE" *J. Immunol.* 151(5):2623-2632 (Sep. 1, 1993).

Pesta, L., "Antibody Engineering" *Curr. Op. Struct. Biol.* 2:593-596 (1992).

Raff, "Social Controls on Cell Survival and Cell Death" *Nature* 356:397-400 (1992).

*Remington's Pharmaceutical Sciences*, Oslo et al., ed., 16th edition, Mack Publishing Co. (1980).

Reyes et al., "Expression of Human β-interferon cDNA Under the Control of a Thymidine Kinase Promoter from Herpes Simplex Virus" *Nature* 297:598-601 (Jun. 17, 1982).

Reichmann et al., "Reshaping Human Antibodies for Therapy" *Nature* 332:323-327 (Mar. 24, 1988).

Ruppert et al., "Cloning and Expression of Human $TAF_{II}250$: a TBP-associated Factor Implicated in Cell-cycle Regulation" *Nature* 362:175-179 (1993).

Sachs et al., "Control of Programmed Cell Death in Normal and Leukemic Cells: New Implications for Therapy" *Blood* 82:15-21 (1993).

Sambrook et al. *Molecular Cloning: A Laboratory Manual*, Second edition, New York:Cold Spring Harbor Laboratory Press (1989).

Schall et al., "Molecular Cloning and Expression of a Receptor for Human Tumor Necrosis Factor" *Cell* 61:361-370 (Apr. 20, 1990).

Schmid et al., "DNA Fragmentation: Manifestation of Target Cell Destruction Mediated by Cytotoxic T-cell Lines, Lymphotoxin-secreting Helper T-cell Clones, and Cell-free Lymphotoxin-containing Supernatant" *Proc. Natl. Acad. Sci. USA* 83:1881-1885 (1986).

Shaw et al., "A General Method for the Transfer of Cloned Genes to Plant Cells" *Gene* 23:315-330 (1983).

Sienbenlist et al., "*E. coli* RNA Polymerase Interacts Homologously with Two Different Promoters" *Cell* 20:269-281 (Jun. 1980).

Sims et al., "A Humanized CD19 Antibody Can Block Function Without Cell Destruction" *The Journal of Immunology* 151(4):2296-2308 (Aug. 1993).

Skinner et al., "Use of the Glu-Glu-Phe C-terminal Epitope for Rapid Purification of the Catalytic Domain of Normal and Mutant ras GTPase-activating Proteins" *Journal of Biological Chemistry* 266:14163-14166 (1991).

Smith et al., "A Receptor for Tumor Necrosis Factor Defines an Unusual Family of Cellular and Viral Proteins" *Science* 248:1019-1023 (May 25, 1990).

Sojar et al., "A Chemical Method for the Deglycosylation of Proteins" *Archives of Biochemical & Biophysics* 259(1):52-57 (1987).

Southern et al., "Transformation of Mammalian Cells to Antibiotic Resistance with a Bacterial Gene Under Control of the SV40 Early Region Prometer" *J. Molec. Appl. Genet.* 1:327-341 (1982).

Steller, "Mechanisms and Genes of Cellular Suicide" *Science* 267:1445-1449 (1995).

Stinchcomb et al., "Isolation and Characterization of a Yeast Chromosomal Replicator" *Nature* 282:39-43 (Nov. 1, 1979).

Suda et al., "Molecular Cloning and Expression of the Fas Ligand, a Novel Member of the Tumor Necrosis Factor Family" *Cell* 75:1169-1178 (1993).

Sugden et al., "A Vector that Replicates as a Plasmid and Can Be Efficiently Selected in B-Lymphoblasts Transformed by Epstein-Barr Virus" *Molecular & Cellular Biology* 5: 410-413 (1985).

Suresh et al., "Bispecific Monoclonal Antibodies from Hybrid Hybridomas" *Methods in Enzymology* 121:210-228 (1986).

Suva et al., "A parathyroid hormane-related protein implicated in malignant hypercemia: cloning and expression" *Science* 237(4817):893-896 (Aug. 1987).

Tanaka et al., "Downregulation of Fas ligand by shedding" *Nature Medicine* 4(1):31-36 (Jan. 1988).

Thomas, P., "Hybridization of Denatured DNA and Small DNA Fragments Transferred to Nitrocellulose" *Proc. Natl. Acad. Sci. USA* 77(9):5201-5205 (Sep. 1980).

Thompson, "Apoptosis in the Pathogenesis and Treatment of Disease" *Science* 267:1456-1462 (1995).

Thotakura et al., "Enzymatic Deglycosylation of Glycoproteins" *Meth. Enzymol.* 138:350-359 (1987).

*Tissue Culture*, Kruse and Patterson, ed., New York: Academic Press (1973).

Traunecker et al., "Bispecific Single Chain Molecules (Janusins) Targets Cytotoxic Lymphocytes on HIV Infected Cells" *EMBO Journal* 10(12):3655-3659 (1991).

Tschumper et al., "Sequence of a Yeast DNA Fragment Containing a Chromosomal Replicator and the TRP1 Gene" *Gene* 10:157-166 (1980).

Tsutsumi et al., "Chemical modification of natural human tumor necrosis factor-alpha with polyethylene glycol increases its anti-tumor potency" *Jap. J. Can. Res.* 85(1):9-12 (Jan. 1994).

Urlaub et al., "Isolation of Chinese Hamster Cell Mutants Deficient in Dihydrofolate Reductase Activity" *Proc. Natl. Acad. Sci. USA* 77(7):4216-4220 (Jul. 1980).

Van den Berg et al., "Kluyveromyces as a Host for Heterologous Gene Expression: Expression and Secretion of Prochymosin" *Bio/Technology* 8:135-139 (1990).

Van Solingen et al., "Fusion of Yeast Spheroplasts" *J. Bact.* 130:946-947 (1977).

Verhoeyen et al., "Reshaping Human Antibodies: Grafting and Antilysozme Activity" *Science* 239:1534-1536 (Mar. 25, 1988).

Watanabe-Fukunaga et al., "Lymphoproliferation Disorder in Mice Explained by Defects in Fas Antigen that Mediates Apoptosis" *Nature* 356:314-317 (1992).

Wiley et al., "Indentification and Characterization of a New Member of the TNF Family that Induces Apoptosis" *Immunity* 3:673-682 (1995).

Yaniv, M., "Enhancing Elements for Activation of Eukaryotic Promoters" *Nature* 297(6):17-18 (May 1982).

Yonehara et al., "A cell-killing monoclonal antibody (anti-Fas) to a cell surface antigen co-downregulated with the receptor of tumor necrosis factor" *Journal of Experimental Medicine* 169:1747-1756 (1989).

Zheng et al., "Induction of Apoptosis in Mature T Cells by Tumor Necrosis Factor"0 *Nature* 377:348-351 (1995).

Zola, "Using Monoclonal Antibodies: Soluble Antigens" *Monoclonal Antibodies: A Manual of Techniques*, CRC Press, Chapter 6, pps. 147-158 (1987).

Zoller et al., "Oligonucleotide-directed Mutagenesis Using M13-derived Vectors: An Efficient and General Procedure for the Production of Point Mutations in Any Fragment of DNA" *Nucl. Acids Res.* 10(20):6487-6500 (1982).

Lawrence et al., "Differential hepatocyte toxicity of recombinant Apo2L/TRAIL versions" *Nature Medicine* 7 (4):383-385 (Apr. 2001).

Qin et al., "Avoiding premature apoposis of normal epideral cells" *Natural Medicine* 7(4):385-386 (Apr. 2001).

Jo et al., "Apoptosis induced in normal human hepatocytes by tumor necrosis factor-related apoptosis-inducing ligand" *Nature Medicine* 6(5):564-567 (May 2000).

Nagata, S., "Steering anti-cancer drugs away from the TRAIL" *Natural Medicine* 6(5):502-503 (May 2000).

* cited by examiner

```
  1  TTTCCTCACTGACTATAAAGAATAGAGAAGGAAGGGCTTCAGTGACCGGCTGCCTGCTGACTACAGCAGTCAGACTCTGACAGGATC

91  ATGGCTATGATGAGTCCAGGGGGACCCAGCCTGGGACAGACCTGCCTGCTGCTGATCGTGATCTTCACAGTGCTCCTGCAGTCTCTGT
  1  MetAlaMetMetGluValGlnGlyGlyProSerLeuGlyGlnThrCysValLeuIleValIlePheThrValLeuLeuGlnSerLeuCys

181  GTGGCTGTAACTTACGTGTACTTTACCAACGAGCTGCAGGACAGAGCTGAAGCAGAGATGCAAGTACTCCAAAAGTGGCATTGCTTGTTTCTTAAAAGAA
 31  ValAlaValThrTyrValTyrPheThrAsnGluLeuLysGlnMetGlnLeuLysGlnAspLysTyrSerLysSerGlyIleAlaCysPheLeuLysGlu

271  GATGACAGTTATTGGGACCCCAATGACGAAGAGAGTATGAACAGCCCCTGCTGGCAAGTGCAACTCCGTCAGCTCGTTAGAAAG
 61  AspAspSerTryTrpAspProAsnAspGluGluSerMetAsnSerProCysTrpGlnValLysTrpGlnLeuArgGlnLeuValArgLys

361  ATGATTTTGAGAACCTCTGAGGAAACCATTCTACAGTTCAAGAAAGCAACAAAAATATTCTCCCCTAGTGAGAGAAACAGGTCCTCAG
 91  MetIleLeuArgThrSerGluGluThrIleSerThrValGlnGluLysGlnAsnIleSerProLeuValArgGluArgGlyProGln
                                                                                    *

451  AGAGTAGCAGCTCACATAACTGGGACCAGAGAAGAACAACATTGTCTTCTCCAAACTCCAAGAATGAAAAGGCTCGGCCGCAAA
121  ArgValAlaAlaHisIleThrGlyThrArgGlyThrArgGlySerAsnThrLeuSerSerProAsnSerLysAsnGluLysAlaLeuGlyArgLys

541  ATAAACTCCTGGAATCATCAAGGAGTGGCATTCATTCCTGAGCAACTTGCACTTGAGGAATGGTCAACTGGTCATCATGAAAAGGG
151  IleAsnSerTrpGluSerSerArgSerGlyHisSerPheLeuSerAsnLeuHisLeuArgAsnGlyGluLeuValIleHisGluLysGly

631  TTTTACTACATCTATTCCCAAACATACTTTCGATTTCAGGAGGAGAAATAAAGAAGAACGACAACAAAGAAAACACAAAATGTCAATATATT
181  PheTyrTyrIleTyrSerGlnThrTyrPheArgPheGlnGluGluIleLysLysGluAsnAspLysAsnThrLysGluAsnMetValGlnTyrIle

721  TACAAATACACAAGTATCCTGACCCTATATTGTTGATGAAAGTGCTAGAAAGTGTGTCTAAAGATGCAGAATATGGACTCTAT
211  TyrLysTyrThrSerTyrProAspProIleLeuLeuMetLysSerAlaArgAsnSerCysTrpSerLysAspAlaGluTyrGlyLeuTyr

811  TCCATCTATCAAGGGGAATATTTGAGCTTAAGGAAATGACAGAATTTTTGTTTCTGTAACAATGACACTTGATGAACATGACCAT
241  SerIleTyrGlnGlyGlyIlePheGluLeuLysGluAsnAspArgIlePheValSerValThrAsnGluHisLeuIleAspMetAspHis

901  GAAGCCAGTTTTTTCGGGGCCTTTTAGTTGGCTAACTGACCTGAAAAGAAAGCAATAACCTCAAAGTGACTATTCAGTTTTCAGGAT
271  GluAlaSerPhePheGlyAlaPheLeuValGlyStp

991  GATACACTATGAAGATGTTTCAAAAATCTGACCAAAAACAACAAACAGAAA
```

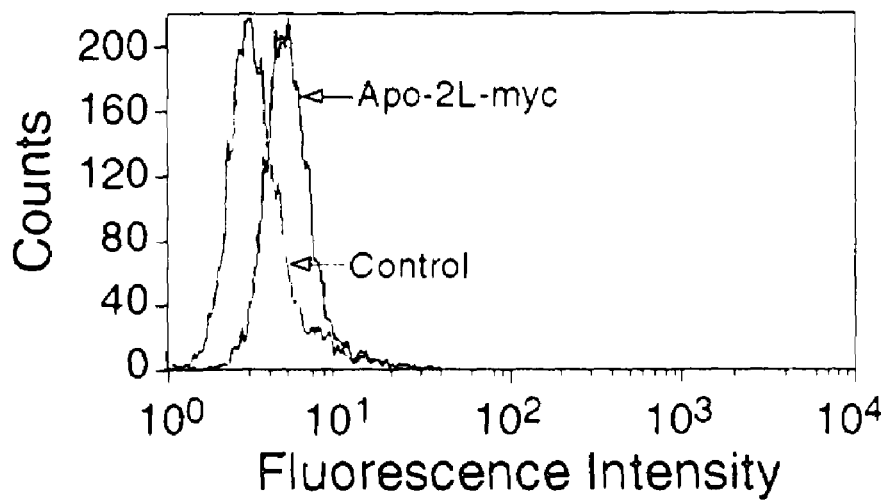
FIG. 1C
FIG. 1D
FIG. 1E

FIG. 2E

SEQUENCE LISTING

<160> NUMBER OF SEQ ID NOS: 17

<210> SEQ ID NO 1
<211> LENGTH: 281
<212> TYPE: PRT
<213> ORGANISM: Homo sapiens

<400> SEQUENCE: 1

| Met | Ala | Met | Met | Glu | Val | Gln | Gly | Gly | Pro | Ser | Leu | Gly | Gln | Thr | Cys |
|---|---|---|---|---|---|---|---|---|---|---|---|---|---|---|---|
| 1 | | | | 5 | | | | | 10 | | | | | 15 | |

| Val | Leu | Ile | Val | Ile | Phe | Thr | Val | Leu | Leu | Gln | Ser | Leu | Cys | Val | Ala |
|---|---|---|---|---|---|---|---|---|---|---|---|---|---|---|---|
| | | | | 20 | | | | | 25 | | | | | 30 | |

| Val | Thr | Tyr | Val | Tyr | Phe | Thr | Asn | Glu | Leu | Lys | Gln | Met | Gln | Asp | Lys |
|---|---|---|---|---|---|---|---|---|---|---|---|---|---|---|---|
| | | | | 35 | | | | | 40 | | | | | 45 | |

| Tyr | Ser | Lys | Ser | Gly | Ile | Ala | Cys | Phe | Leu | Lys | Glu | Asp | Ser | Tyr |
|---|---|---|---|---|---|---|---|---|---|---|---|---|---|---|
| | 50 | | | | | 55 | | | | | 60 | | | |

| Trp | Asp | Pro | Asn | Asp | Glu | Glu | Ser | Met | Asn | Ser | Pro | Cys | Trp | Gln | Val |
|---|---|---|---|---|---|---|---|---|---|---|---|---|---|---|---|
| 65 | | | | | 70 | | | | | 75 | | | | | 80 |

| Lys | Trp | Gln | Leu | Arg | Gln | Leu | Val | Arg | Lys | Met | Ile | Leu | Arg | Thr | Ser |
|---|---|---|---|---|---|---|---|---|---|---|---|---|---|---|---|
| | | | | 85 | | | | | 90 | | | | | 95 | |

| Glu | Glu | Thr | Ile | Ser | Thr | Val | Gln | Glu | Lys | Gln | Gln | Asn | Ile | Ser | Pro |
|---|---|---|---|---|---|---|---|---|---|---|---|---|---|---|---|
| | | | | 100 | | | | | 105 | | | | | 110 | |

| Leu | Val | Arg | Glu | Arg | Gly | Pro | Gln | Arg | Val | Ala | Ala | His | Ile | Thr | Gly |
|---|---|---|---|---|---|---|---|---|---|---|---|---|---|---|---|
| | | | | 115 | | | | | 120 | | | | | 125 | |

| Thr | Arg | Gly | Arg | Ser | Asn | Thr | Leu | Ser | Ser | Pro | Asn | Ser | Lys | Asn | Glu |
|---|---|---|---|---|---|---|---|---|---|---|---|---|---|---|---|
| | 130 | | | | | 135 | | | | | 140 | | | | |

| Lys | Ala | Leu | Gly | Arg | Lys | Ile | Asn | Ser | Trp | Glu | Ser | Ser | Arg | Ser | Gly |
|---|---|---|---|---|---|---|---|---|---|---|---|---|---|---|---|
| 145 | | | | | 150 | | | | | 155 | | | | | 160 |

| His | Ser | Phe | Leu | Ser | Asn | Leu | His | Leu | Arg | Asn | Gly | Glu | Leu | Val | Ile |
|---|---|---|---|---|---|---|---|---|---|---|---|---|---|---|---|
| | | | | 165 | | | | | 170 | | | | | 175 | |

| His | Glu | Lys | Gly | Phe | Tyr | Tyr | Ile | Tyr | Ser | Gln | Thr | Tyr | Phe | Arg | Phe |
|---|---|---|---|---|---|---|---|---|---|---|---|---|---|---|---|
| | | | | 180 | | | | | 185 | | | | | 190 | |

| Gln | Glu | Glu | Ile | Lys | Glu | Asn | Thr | Lys | Asn | Asp | Lys | Gln | Met | Val | Gln |
|---|---|---|---|---|---|---|---|---|---|---|---|---|---|---|---|
| | | | | 195 | | | | | 200 | | | | | 205 | |

| Tyr | Ile | Tyr | Lys | Tyr | Thr | Ser | Tyr | Pro | Asp | Pro | Ile | Leu | Leu | Met | Lys |
|---|---|---|---|---|---|---|---|---|---|---|---|---|---|---|---|
| 210 | | | | | 215 | | | | | 220 | | | | | |

| Ser | Ala | Arg | Asn | Ser | Cys | Trp | Ser | Lys | Asp | Ala | Glu | Tyr | Gly | Leu | Tyr |
|---|---|---|---|---|---|---|---|---|---|---|---|---|---|---|---|
| 225 | | | | | 230 | | | | | 235 | | | | | 240 |

| Ser | Ile | Tyr | Gln | Gly | Gly | Ile | Phe | Glu | Leu | Lys | Glu | Asn | Asp | Arg | Ile |
|---|---|---|---|---|---|---|---|---|---|---|---|---|---|---|---|
| | | | | 245 | | | | | 250 | | | | | 255 | |

| Phe | Val | Ser | Val | Thr | Asn | Glu | His | Leu | Ile | Asp | Met | Asp | His | Glu | Ala |
|---|---|---|---|---|---|---|---|---|---|---|---|---|---|---|---|
| | | | | 260 | | | | | 265 | | | | | 270 | |

| Ser | Phe | Phe | Gly | Ala | Phe | Leu | Val | Gly |
|---|---|---|---|---|---|---|---|---|
| | 275 | | | | | 280 | | |

<210> SEQ ID NO 2
<211> LENGTH: 1042
<212> TYPE: DNA
<213> ORGANISM: Homo sapiens

<400> SEQUENCE: 2
tttcctcact gactataaaa gaatagagaa ggaagggctt cagtgaccgg ctgcctggct      60
gacttacagc agtcagactc tgacaggatc atggctatga tggaggtcca gggggggaccc     120 agcctgggac agacctgcgt gctgatcgtg atcttcacag tgctcctgca gtctctctgt     180

```
gtggctgtaa cttacgtgta ctttaccaac gagctgaagc agatgcagga caagtactcc      240
aaaagtggca ttgcttgttt cttaaaagaa gatgacagtt attgggaccc caatgacgaa      300
gagagtatga acagccctg ctggcaagtc aagtggcaac tccgtcagct cgttagaaag       360
atgattttga gaacctctga ggaaaccatt tctacagttc aagaaaagca acaaaatatt      420
tctcccctag tgagagaaag aggtcctcag agagtagcag ctcacataac tgggaccaga      480
ggaagaagca acacattgtc ttctccaaac tccaagaatg aaaaggctct gggccgcaaa      540
ataaactcct gggaatcatc aaggagtggg cattcattcc tgagcaactt gcacttgagg      600
aatggtgaac tggtcatcca tgaaaaggg ttttactaca tctattccca acatactttt       660
cgatttcagg aggaaataaa agaaaacaca agaacgaca acaaatggt ccaatatatt        720 tacaaataca caagttatcc tgaccctata ttgttgatga aaagtgctag aaatagttgt      780
tggtctaaag atgcagaata tggactctat tccatctatc aagggggaat atttgagctt     840
aaggaaaatg acagaatttt tgtttctgta acaaatgagc acttgataga catggaccat     900
gaagccagtt ttttcgggge cttttagtt ggctaactga cctggaaaga aaagcaata     960 acctcaaagt gactattcag ttttcaggat gatacactat gaagatgttt caaaaaatct   1020
gaccaaaaca aacaaacaga aa                                            1042

<210> SEQ ID NO 3
<211> LENGTH: 390
<212> TYPE: DNA
<213> ORGANISM: Homo sapiens

<400> SEQUENCE: 3
gggaccccaa tgacgaagag agtatgaaca gcccctgctg gcaagtcaag tggcaactcc      60
gtcagctcgt tagaaagatg attttgagaa cctctgagga aaccatttct acagttcaag     120
aaaagcaaca aaatatttct cccctagtga gagaaagagg tcctcagaga gtagcagctc     180
acataactgg gaccagagga agaagcaaca cattgtcttc tccaaactcc aagaatgaaa     240
aggctctggg ccgcaaaata aactcctggg aatcatcaag gagtgggcat tcattcctga     300
gcaacttgca cttgaggaat ggtgaactgg tcatccatga aaaagggttt tactacatct     360
attcccaaac atactttcga tttcaggagg                                      390

<210> SEQ ID NO 4
<211> LENGTH: 60
<212> TYPE: DNA
<213> ORGANISM: Artificial Sequence
<220> FEATURE:
<221> NAME/KEY: misc_feature
<222> LOCATION: (1)..(60)
<223> OTHER INFORMATION: Sequence is synthesized

<400> SEQUENCE: 4
tgacgaagag agtatgaaca gcccctgctg gcaagtcaag tggcaactcc gtcagctcgt      60

<210> SEQ ID NO 5
<211> LENGTH: 60
<212> TYPE: DNA
<213> ORGANISM: Artificial Sequence
<220> FEATURE:
<221> NAME/KEY: misc_feature
<222> LOCATION: (1)..(60)
<223> OTHER INFORMATION: Sequence is synthesized

<400> SEQUENCE: 5
```
ggtgaactgg tcatccatga aaagggttt tactacatct attcccaaac atactttcga     60

<210> SEQ ID NO 6
<211> LENGTH: 13
<212> TYPE: PRT
<213> ORGANISM: Artificial Sequence
<220> FEATURE:
<221> NAME/KEY: UNSURE
<222> LOCATION: (1)..(13)
<223> OTHER INFORMATION: Sequence is synthesized

<400> SEQUENCE: 6

```
Ser Met Glu Gln Lys Leu Ile Ser Glu Glu Asp Leu Asn
 1               5                  10
```

<210> SEQ ID NO 7
<211> LENGTH: 27
<212> TYPE: PRT
<213> ORGANISM: Artificial Sequence
<220> FEATURE:
<221> NAME/KEY: UNSURE
<222> LOCATION: (1)..(27)
<223> OTHER INFORMATION: Sequence is synthesized

<400> SEQUENCE: 7

```
Lys Tyr Ala Leu Ala Asp Ala Ser Leu Lys Met Ala Asp Pro Asn Arg
 1               5                  10                  15

Phe Arg Gly Lys Asp Leu Pro Val Leu Asp Gln
            20                  25
```

<210> SEQ ID NO 8
<211> LENGTH: 24
<212> TYPE: PRT
<213> ORGANISM: Artificial Sequence
<220> FEATURE:
<221> NAME/KEY: UNSURE
<222> LOCATION: (1)..(24)
<223> OTHER INFORMATION: Sequence is synthesized

<400> SEQUENCE: 8

```
Met Gly His His His His His His His His His Ser Ser Gly His
 1               5                  10                  15

Ile Asp Asp Asp Asp Lys His Met
            20
```

<210> SEQ ID NO 9
<211> LENGTH: 175
<212> TYPE: PRT
<213> ORGANISM: Homo sapiens

<400> SEQUENCE: 9

```
Asp Pro Ala Gly Leu Leu Asp Leu Arg Gln Gly Met Phe Ala Gln Leu
 1               5                  10                  15

Val Ala Gln Asn Val Leu Leu Ile Asp Gly Pro Leu Ser Trp Tyr Ser
            20                  25                  30

Asp Pro Gly Leu Ala Gly Val Ser Leu Thr Gly Gly Leu Ser Tyr Lys
        35                  40                  45

Glu Asp Thr Lys Glu Leu Val Val Ala Lys Ala Gly Val Tyr Tyr Val
    50                  55                  60

Phe Phe Gln Leu Glu Leu Arg Arg Val Val Ala Gly Glu Gly Ser Gly
65                  70                  75                  80

Ser Val Ser Leu Ala Leu His Leu Gln Pro Leu Arg Ser Ala Ala Gly
                85                  90                  95
```

```
Ala Ala Ala Leu Ala Leu Thr Val Asp Leu Pro Ala Ser Ser Glu
            100                 105                 110

Ala Arg Asn Ser Ala Phe Gly Phe Gln Gly Arg Leu Leu His Leu Ser
            115                 120                 125

Ala Gly Gln Arg Leu Gly Val His Leu His Thr Glu Ala Arg Ala Arg
        130                 135                 140

His Ala Trp Gln Leu Thr Gln Gly Ala Thr Val Leu Gly Leu Phe Arg
145                 150                 155                 160

Val Thr Pro Glu Ile Pro Ala Gly Leu Pro Ser Pro Arg Ser Glu
                165                 170                 175

<210> SEQ ID NO 10
<211> LENGTH: 132
<212> TYPE: PRT
<213> ORGANISM: Homo sapiens

<400> SEQUENCE: 10

Val Ser His Arg Tyr Pro Arg Ile Gln Ser Ile Lys Val Gln Phe Thr
1               5                   10                  15

Glu Tyr Lys Lys Glu Lys Gly Phe Ile Leu Thr Ser Gln Lys Glu Asp
            20                  25                  30

Glu Ile Met Lys Val Gln Asn Asn Ser Val Ile Ile Asn Cys Asp Gly
        35                  40                  45

Phe Tyr Leu Ile Ser Leu Lys Gly Tyr Phe Ser Gln Glu Val Asn Ile
    50                  55                  60

Ser Leu His Tyr Gln Lys Asp Glu Glu Pro Leu Phe Gln Leu Lys Lys
65                  70                  75                  80

Val Arg Ser Val Asn Ser Leu Met Val Ala Ser Leu Thr Tyr Lys Asp
                85                  90                  95

Lys Val Tyr Leu Asn Val Thr Thr Asp Asn Thr Ser Leu Asp Asp Phe
            100                 105                 110

His Val Asn Gly Gly Glu Leu Ile Leu Ile His Gln Asn Pro Gly Glu
        115                 120                 125

Phe Cys Val Leu
    130

<210> SEQ ID NO 11
<211> LENGTH: 151
<212> TYPE: PRT
<213> ORGANISM: Homo sapiens

<400> SEQUENCE: 11

Gln Gln Gln Leu Pro Leu Glu Ser Leu Gly Trp Asp Val Ala Glu Leu
1               5                   10                  15

Gln Leu Asn His Thr Gly Pro Gln Gln Asp Pro Arg Leu Tyr Trp Gln
            20                  25                  30

Gly Gly Pro Ala Leu Gly Arg Ser Phe Leu His Gly Pro Glu Leu Asp
        35                  40                  45

Lys Gly Gln Leu Arg Ile His Arg Asp Gly Ile Tyr Met Val His Ile
    50                  55                  60

Gln Val Thr Leu Ala Ile Cys Ser Ser Thr Thr Ala Ser Arg His His
65                  70                  75                  80

Pro Thr Thr Leu Ala Val Gly Ile Cys Ser Pro Ala Ser Arg Ser Ile
                85                  90                  95

Ser Leu Leu Arg Leu Ser Phe His Phe His Gln Gly Cys Thr Ile Val
            100                 105                 110
```

```
Ser Gln Arg Leu Thr Pro Leu Ala Arg Gly Asp Thr Leu Cys Thr Asn
        115                 120                 125
Leu Thr Gly Thr Leu Leu Pro Ser Arg Asn Thr Asp Glu Thr Phe Phe
130                 135                 140
Gly Val Gln Trp Val Arg Pro
145                 150

<210> SEQ ID NO 12
<211> LENGTH: 148
<212> TYPE: PRT
<213> ORGANISM: Homo sapiens

<400> SEQUENCE: 12

Leu Cys Ile Leu Lys Arg Ala Pro Phe Lys Lys Ser Trp Ala Tyr Leu
1               5                   10                  15
Gln Val Ala Lys His Leu Asn Lys Thr Lys Leu Ser Trp Asn Lys Asp
            20                  25                  30
Gly Ile Leu His Gly Val Arg Tyr Gln Asp Gly Asn Leu Val Ile Gln
        35                  40                  45
Phe Pro Gly Leu Tyr Phe Ile Ile Cys Gln Leu Gln Phe Leu Val Gln
    50                  55                  60
Cys Pro Asn Asn Ser Val Asp Leu Lys Leu Glu Leu Leu Ile Asn Lys
65                  70                  75                  80
His Ile Lys Lys Gln Ala Leu Val Thr Val Cys Glu Ser Gly Met Gln
                85                  90                  95
Thr Lys His Val Tyr Gln Asn Leu Ser Gln Phe Leu Leu Asp Tyr Leu
            100                 105                 110
Gln Val Asn Thr Thr Ile Ser Val Asn Val Asp Thr Phe Gln Tyr Ile
        115                 120                 125
Asp Thr Ser Thr Phe Pro Leu Glu Asn Val Leu Ser Ile Phe Leu Tyr
    130                 135                 140
Ser Asn Ser Asp
145

<210> SEQ ID NO 13
<211> LENGTH: 157
<212> TYPE: PRT
<213> ORGANISM: Homo sapiens

<400> SEQUENCE: 13

Val Arg Ser Ser Arg Thr Pro Ser Asp Lys Pro Val Ala His Val Val
1               5                   10                  15
Val Ala Asn Pro Gln Ala Glu Gly Gln Leu Gln Trp Leu Asn Arg Arg
            20                  25                  30
Ala Asn Ala Leu Leu Ala Asn Gly Val Glu Leu Arg Asp Asn Gln Leu
        35                  40                  45
Val Val Pro Ser Glu Gly Leu Tyr Leu Ile Tyr Ser Gln Val Leu Phe
    50                  55                  60
Lys Gly Gln Gly Cys Pro Ser Thr His Val Leu Leu Thr His Thr Ile
65                  70                  75                  80
Ser Arg Ile Ala Val Ser Tyr Gln Thr Lys Val Asn Leu Leu Ser Ala
                85                  90                  95
Ile Lys Ser Pro Cys Gln Arg Glu Thr Pro Glu Gly Ala Glu Ala Lys
            100                 105                 110
Pro Trp Tyr Glu Pro Ile Tyr Leu Gly Gly Val Phe Gln Leu Glu Lys
        115                 120                 125
```

```
Gly Asp Arg Leu Ser Ala Glu Ile Asn Arg Pro Asp Tyr Leu Asp Phe
            130                 135                 140

Ala Glu Ser Gly Gln Val Tyr Phe Gly Ile Ile Ala Leu
145                 150                 155

<210> SEQ ID NO 14
<211> LENGTH: 168
<212> TYPE: PRT
<213> ORGANISM: Homo sapiens

<400> SEQUENCE: 14

Glu Glu Pro Glu Thr Asp Leu Ser Pro Gly Leu Pro Ala Ala His Leu
  1               5                  10                  15

Ile Gly Ala Pro Leu Lys Gly Gln Gly Leu Gly Trp Glu Thr Thr Lys
                 20                  25                  30

Glu Gln Ala Phe Leu Thr Ser Gly Thr Gln Phe Ser Asp Ala Glu Gly
             35                  40                  45

Leu Ala Leu Pro Gln Asp Gly Leu Tyr Tyr Leu Tyr Cys Leu Val Gly
 50                  55                  60

Tyr Arg Gly Arg Ala Pro Pro Gly Gly Asp Pro Gln Gly Arg Ser
 65                  70                  75                  80

Val Thr Leu Arg Ser Ser Leu Tyr Arg Ala Gly Gly Ala Tyr Gly Pro
                 85                  90                  95

Gly Thr Pro Glu Leu Leu Leu Glu Gly Ala Glu Thr Val Thr Pro Val
            100                 105                 110

Leu Asp Pro Ala Arg Arg Gln Gly Tyr Gly Pro Leu Trp Tyr Thr Ser
            115                 120                 125

Val Gly Phe Gly Gly Leu Val Gln Leu Arg Arg Gly Glu Arg Val Tyr
130                 135                 140

Val Asn Ile Ser His Pro Asp Met Tyr Asp Phe Ala Arg Gly Lys Thr
145                 150                 155                 160

Phe Phe Gly Ala Val Met Val Gly
                165

<210> SEQ ID NO 15
<211> LENGTH: 155
<212> TYPE: PRT
<213> ORGANISM: Homo sapiens

<400> SEQUENCE: 15

Pro Lys Met His Leu Ala His Ser Thr Leu Lys Pro Ala Ala His Leu
  1               5                  10                  15

Ile Gly Asp Pro Ser Lys Gln Asn Ser Leu Leu Trp Arg Ala Asn Thr
                 20                  25                  30

Asp Arg Ala Phe Leu Gln Asp Gly Phe Ser Leu Ser Asn Asn Ser Leu
             35                  40                  45

Leu Val Pro Thr Ser Gly Ile Tyr Phe Val Tyr Ser Gln Val Val Phe
 50                  55                  60

Ser Gly Lys Ala Tyr Ser Pro Lys Ala Thr Ser Ser Pro Leu Tyr Leu
 65                  70                  75                  80

Ala His Glu Val Gln Leu Phe Ser Ser Gln Tyr Pro Phe His Val Pro
                 85                  90                  95

Leu Leu Ser Ser Gln Lys Met Val Tyr Pro Gly Leu Gln Glu Pro Trp
            100                 105                 110

Leu His Ser Met Tyr His Gly Ala Ala Phe Gln Leu Thr Gln Gly Asp
            115                 120                 125
```

-continued

```
Gln Leu Ser Thr His Thr Asp Gly Ile Pro His Leu Val Leu Ser Pro
        130                 135                 140

Ser Thr Val Val Phe Phe Gly Ala Phe Ala Leu
145                 150                 155

<210> SEQ ID NO 16
<211> LENGTH: 149
<212> TYPE: PRT
<213> ORGANISM: Homo sapiens

<400> SEQUENCE: 16

Met Gln Lys Gly Asp Gln Asn Pro Gln Ile Ala Ala His Val Ile Ser
  1               5                  10                  15

Glu Ala Ser Ser Lys Thr Thr Ser Val Leu Gln Trp Ala Glu Lys Gly
                 20                  25                  30

Tyr Tyr Thr Met Ser Asn Asn Leu Val Thr Leu Glu Asn Gly Lys Gln
             35                  40                  45

Leu Thr Val Lys Arg Gln Gly Leu Tyr Tyr Ile Tyr Ala Gln Val Thr
         50                  55                  60

Phe Cys Ser Asn Arg Glu Ala Ser Ser Gln Ala Pro Phe Ile Ala Ser
 65                  70                  75                  80

Leu Cys Leu Lys Ser Pro Gly Arg Phe Glu Arg Ile Leu Leu Arg Ala
                 85                  90                  95

Ala Asn Thr His Ser Ser Ala Lys Pro Cys Gly Gln Gln Ser Ile His
            100                 105                 110

Leu Gly Gly Val Phe Glu Leu Gln Pro Gly Ala Ser Val Phe Val Asn
        115                 120                 125

Val Thr Asp Pro Ser Gln Val Ser His Gly Thr Gly Phe Thr Ser Phe
    130                 135                 140

Gly Leu Leu Lys Leu
145

<210> SEQ ID NO 17
<211> LENGTH: 149
<212> TYPE: PRT
<213> ORGANISM: Homo sapiens

<400> SEQUENCE: 17

Pro Ser Pro Pro Pro Glu Lys Lys Glu Leu Arg Lys Val Ala His Leu
  1               5                  10                  15

Thr Gly Lys Ser Asn Ser Arg Ser Met Pro Leu Glu Trp Glu Asp Thr
                 20                  25                  30

Tyr Gly Ile Val Val Leu Leu Ser Gly Val Lys Tyr Lys Lys Gly Gly
             35                  40                  45

Leu Val Ile Asn Glu Thr Gly Leu Tyr Phe Val Tyr Ser Lys Val Tyr
         50                  55                  60

Phe Arg Gly Gln Ser Cys Asn Asn Leu Pro Leu Ser His Lys Val Tyr
 65                  70                  75                  80

Met Arg Asn Ser Lys Tyr Pro Gln Asp Leu Val Met Met Glu Gly Lys
                 85                  90                  95

Met Met Ser Tyr Cys Thr Thr Gly Gln Met Trp Ala Arg Ser Ser Tyr
            100                 105                 110

Leu Gly Ala Val Phe Asn Leu Thr Ser Ala Asp His Leu Tyr Val Asn
        115                 120                 125
```

```
Val Ser Glu Leu Ser Leu Val Asn Phe Glu Glu Ser Gln Thr Phe Phe
    130                 135                 140

Gly Leu Tyr Lys Leu
145
```

APO-2 LIGAND

This is a continuation of application Ser. No.08/584,031 filed on Jan. 9, 1996 now U.S. Pat. No. 6,030,945, which application is incorporated herein by reference and to which application priority is claimed under 35 USC § 120.

FIELD OF THE INVENTION

The present invention relates generally to the identification, isolation, and recombinant production of a novel cytokine, designated herein as "Apo-2 ligand", which induces mammalian cell apoptosis, and to methods of using Apo-2 ligand.

BACKGROUND OF THE INVENTION

Control of cell numbers in mammals is believed to be determined, in part, by a balance between cell proliferation and cell death. One form of cell death, sometimes referred to as necrotic cell death, is typically characterized as a pathologic form of cell death resulting from some trauma or cellular injury. In contrast, there is another, "physiologic" form of cell death which usually proceeds in an orderly or controlled manner. This orderly or controlled form of cell death is often referred to as "apoptosis" [see, e.g., Barr et al., Bio/Technology, 12:487–493 (1994)]. Apoptotic cell death naturally occurs in many physiological processes, including embryonic development and clonal selection in the immune system [Itoh et al., Cell, 66:233–243 (1991)]. Decreased levels of apoptotic cell death, however, have been associated with a variety of pathological conditions, including cancer, lupus, and herpes virus infection [Thompson, Science, 267: 1456–1462 (1995)].

Apoptotic cell death is typically accompanied by one or more characteristic morphological and biochemical changes in cells, such as condensation of cytoplasm, loss of plasma membrane microvilli, segmentation of the nucleus, degradation of chromosomal DNA or loss of mitochondrial function. A variety of extrinsic and intrinsic signals are believed to trigger or induce such morphological and biochemical cellular changes [Raff, Nature, 356:397–400 (1992); Steller, Science, 267:1445–1449 (1995); Sachs et al., Blood, 82:15 (1993)]. For instance, they can be triggered by hormonal stimuli, such as glucocorticoid hormones for immature thymocytes, as well as withdrawal of certain growth factors [Watanabe-Fukunaga et al., Nature, 356:314–317 (1992)]. Also, some identified oncogenes such as myc, rel, and E1A, and tumor suppressors, like p53, have been reported to have a role in inducing apoptosis. Certain chemotherapy drugs and some forms of radiation have likewise been observed to have apoptosis-inducing activity [Thompson, supra].

Various molecules, such as tumor necrosis factor-α ("TNF-α"), tumor necrosis factor-β ("TNF-β" or "lymphotoxin"), CD30 ligand, CD27 ligand, CD40 ligand, OX-40 ligand, 4-1BB ligand, and Apo-1 ligand (also referred to as Fas ligand or CD95 ligand) have been identified as members of the tumor necrosis factor ("TNF") family of cytokines [See, e.g., Gruss and Dower, Blood, 85:3378–3404 (1995)]. Among these molecules, TNF-α, TNF-β, CD30 ligand, 4-1BB ligand, and Apo-1 ligand have been reported to be involved in apoptotic cell death. Both TNF-α and TNF-β have been reported to induce apoptotic death in susceptible tumor cells [Schmid et al., Proc. Natl. Acad. Sci., 83:1881 (1986); Dealtry et al., Eur. J. Immunol., 17:689 (1987)]. Zheng et al. have reported that TNF-α is involved in post-stimulation apoptosis of CD8-positive T cells [Zheng et al., Nature, 377:348–351 (1995)]. Other investigators have reported that CD30 ligand may be involved in deletion of self-reactive T cells in the thymus [Amakawa et al., Cold Spring Harbor Laboratory Symposium on Programmed Cell Death, Abstr. No. 10, (1995)].

Mutations in the mouse Fas/Apo-1 receptor or ligand genes (called lpr and gld, respectively) have been associated with some autoimmune disorders, indicating that Apo-1 ligand may play a role in regulating the clonal deletion of self-reactive lymphocytes in the periphery [Krammer et al., Curr. Op. Immunol., 6:279–289 (1994); Nagata et al., Science, 267:1449–1456 (1995)]. Apo-1 ligand is also reported to induce post-stimulation apoptosis in CD4-positive T lymphocytes and in B lymphocytes, and may be involved in the elimination of activated lymphocytes when their function is no longer needed, [Krammer et al., supra; Nagata et al., supra]. Agonist mouse monoclonal antibodies specifically binding to the Apo-1 receptor have been reported to exhibit cell killing activity that is comparable to or similar to that of TNF-α [Yonehara et al., J. Exp. Med., 169: 1747–1756 (1989)].

Induction of various cellular responses mediated by such TNF family cytokines is believed to be initiated by their binding to specific cell receptors. Two distinct TNF receptors of approximately 55-kDa (TNF-R1) and 75-kDa (TNF-R2) have been identified [Hohman et al., J. Biol. Chem., 264:14927–14934 (1989); Brockhaus et al., Proc. Natl. Acad. Sci., 87:3127–3131 (1990); EP 417,563, published Mar. 20, 1991] and human and mouse cDNAs corresponding to both receptor types have been isolated and characterized [Loetscher et al., Cell, 61:351 (1990); Schall et al., Cell, 61:361 (1990); Smith et al., Science, 248:1019–1023 (1990); Lewis et al., Proc. Natl. Acad. Sci., 88:2830–2834 (1991); Goodwin et al., Mol. Cell. Biol., 11:3020–3026 (1991)].

Itoh et al. disclose that the Apo-1 receptor can signal an apoptotic cell death similar to that signaled by the 55-kDa TNF-R1 [Itoh et al., supra]. Expression of the Apo-1 antigen has also been reported to be down-regulated along with that of TNF-R1 when cells are treated with either TNF-α or anti-Apo-1 mouse monoclonal antibody [Krammer et al., supra; Nagata et al., supra]. Accordingly, some investigators have hypothesized that cell lines that co-express both Apo-1 and TNF-R1 receptors may mediate cell killing through common signaling pathways [Id.].

The TNF family ligands identified to date, with the exception of lymphotoxin-α, are type II transmembrane proteins, whose C-terminus is extracellular. In contrast, the receptors in the TNF receptor (TNFR) family identified to date are type I transmembrane proteins. In both the TNF ligand and receptor families, however, homology identified between family members has been found mainly in the extracellular domain ("ECD"). Several of the TNF family cytokines, including TNF-α, Apo-1 ligand and CD40 ligand, are cleaved proteolytically at the cell surface; the resulting protein in each case typically forms a homotrimeric molecule that functions as a soluble cytokine. TNF receptor family proteins are also usually cleaved proteolytically to release soluble receptor ECDs that can function as inhibitors of the cognate cytokines. For a review of the TNF family of cytokines and their receptors, see Gruss and Dower, supra.

SUMMARY OF THE INVENTION

Applicants have identified cDNA clones that encode a novel cytokine, designated "Apo-2 ligand." It is presently believed that Apo-2 ligand is a member of the TNF cytokine family; Apo-2 ligand is related in amino acid sequence to some known TNF-related proteins, including the Apo-1 ligand. Applicants found, however, that the Apo-2 ligand is not inhibited appreciably by known soluble Apo-1 or TNF receptors, such as the Fas/Apo-1, TNF-R1, or TNF-R2 receptors.

In one embodiment, the invention provides isolated biologically active Apo-2 ligand. In particular, the invention provides isolated biologically active human Apo-2 ligand, which in one embodiment, includes an amino acid sequence comprising residues 114–281 of FIG. 1A. In another embodiment, the Apo-2 ligand includes an amino acid sequence comprising residues 41–281 or 15–281 of FIG. 1A. In another embodiment, the isolated biologically active human Apo-2 ligand includes an amino acid sequence shown as residues 1–281 of FIG. 1A (SEQ ID NO:1).

In another embodiment, the invention provides chimeric molecules comprising Apo-2 ligand fused to another, heterologous polypeptide. An example of such a chimeric molecule comprises the Apo-2 ligand fused to a tag polypeptide sequence.

In another embodiment, the invention provides an isolated nucleic acid molecule encoding Apo-2 ligand. In one aspect, the nucleic acid molecule is RNA or DNA that encodes a biologically active Apo-2 ligand or is complementary to nucleic acid sequence encoding such Apo-2 ligand, and remains stably bound to it under stringent conditions. In one embodiment, the nucleic acid sequence is selected from:

(a) the coding region of the nucleic acid sequence of FIG. 1A that codes for the full-length protein from residue 1 to residue 281 (i.e., nucleotides 91 through 933), inclusive, or nucleotides 211 through 933 that encodes for the extracellular protein from residue 41 to 281, inclusive, or nucleotides 430 through 933 that encodes for the extracellular protein from residue 114 to 281, inclusive, of the nucleic acid sequence shown in FIG. 1A (SEQ ID NO:2); or (b) a sequence corresponding to the sequence of (a) within the scope of degeneracy of the genetic code.

In a further embodiment, the invention provides a replicable vector comprising the nucleic acid molecule encoding the Apo-2 ligand operably linked to control sequences recognized by a host cell transfected or transformed with the vector. A host cell comprising the vector or the nucleic acid molecule is also provided. A method of producing Apo-2 ligand which comprises culturing a host cell comprising the nucleic acid molecule and recovering the protein from the host cell culture is further provided.

In another embodiment, the invention provides an antibody which binds to the Apo-2 ligand.

In another embodiment, the invention provides a composition comprising biologically active Apo-2 ligand and a pharmaceutically-acceptable carrier. The composition may be a pharmaceutical composition useful for inducing or stimulating apoptosis.

In another embodiment, the invention provides a method for inducing apoptosis in mammalian cells, comprising exposing mammalian cells, in vivo or ex vivo, to an amount of Apo-2 ligand effective for inducing apoptosis.

In another embodiment, the invention provides methods of treating a mammal having cancer. In the methods, an effective amount of Apo-2 ligand is administered to a mammal diagnosed as having cancer. The Apo-2 ligand may also be administered to the mammal along with one or more other therapies, such as chemotherapy, radiation therapy, or other agents capable of inducing apoptosis.

A further embodiment of the invention provides articles of manufacture and kits that include Apo-2 ligand or Apo-2 ligand antibodies. The articles of manufacture and kits include a container, a label on the container, and a composition contained within the container. The label on the container indicates that the composition can be used for certain therapeutic or non-therapeutic applications. The composition contains an active agent, and the active agent comprises Apo-2 ligand or Apo-2 ligand antibodies.

BRIEF DESCRIPTION OF THE DRAWINGS

FIG. 1A shows the nucleotide sequence of hu Apo-2 ligand cDNA (SEQ ID NO:2) and its derived amino acid sequence (SEQ ID NO:1).

FIG. 1B shows an alignment of the C-terminal region of human Apo-2 ligand (Apo2L amino acids 114–281 of SEQ ID NO:1) with the corresponding regions of known members of the human TNF cytokine family, 4-1BBL, (SEQ ID NO: 9) OX40L (SEQ IN NO:10), CD27L (SEQ ID NO: 11), CD30L (SEQ ID NO: 12), TNF-α, (SEQ ID NO: 13) LT-β(SEQ ID NO: 14), LT-α(SEQ ID NO: 15), CD40L (SEQ ID NO: 16), and Apo-1L (SEQ ID NO: 17).

FIGS. 1C–1E show (C) the cellular topology of the recombinant, full-length, C-terminal myc epitope-tagged Apo-2 ligand expressed in human 293 cells, as determined by FACS analysis using anti-epitope antibody; (D) the size and subunit structure of recombinant, $His_{10}$ epitope-tagged soluble Apo-2 expressed in recombinant baculovirus-infected insect cells and purified by $Ni^{2+}$-chelate affinity chromatography, as determined with (lanes 2, 3) or without (lane 1) chemical crosslinking followed by SDS-PAGE and silver staining; (E) the size and subunit structure of recombinant, gD epitope-tagged, soluble Apo-2 ligand expressed in metabolically labeled human 293 cells, as determined by immunoprecipitation with anti-epitope antibody, followed by SDS-PAGE and autoradiography.

FIGS. 2A–2E show the induction of apoptosis in B and T lymphocyte cell lines by Apo-2 ligand. Apoptotic cells were identified by characteristic morphological changes (A); by positive fluorescence staining with propidium iodide (PI) and FITC-conjugated annexin V, measured by flow cytometry (B-D); and by analysis of internucleosomal DNA fragmentation (E).

DETAILED DESCRIPTION OF THE PREFERRED EMBODIMENTS

I. Definitions

Figure 1B:
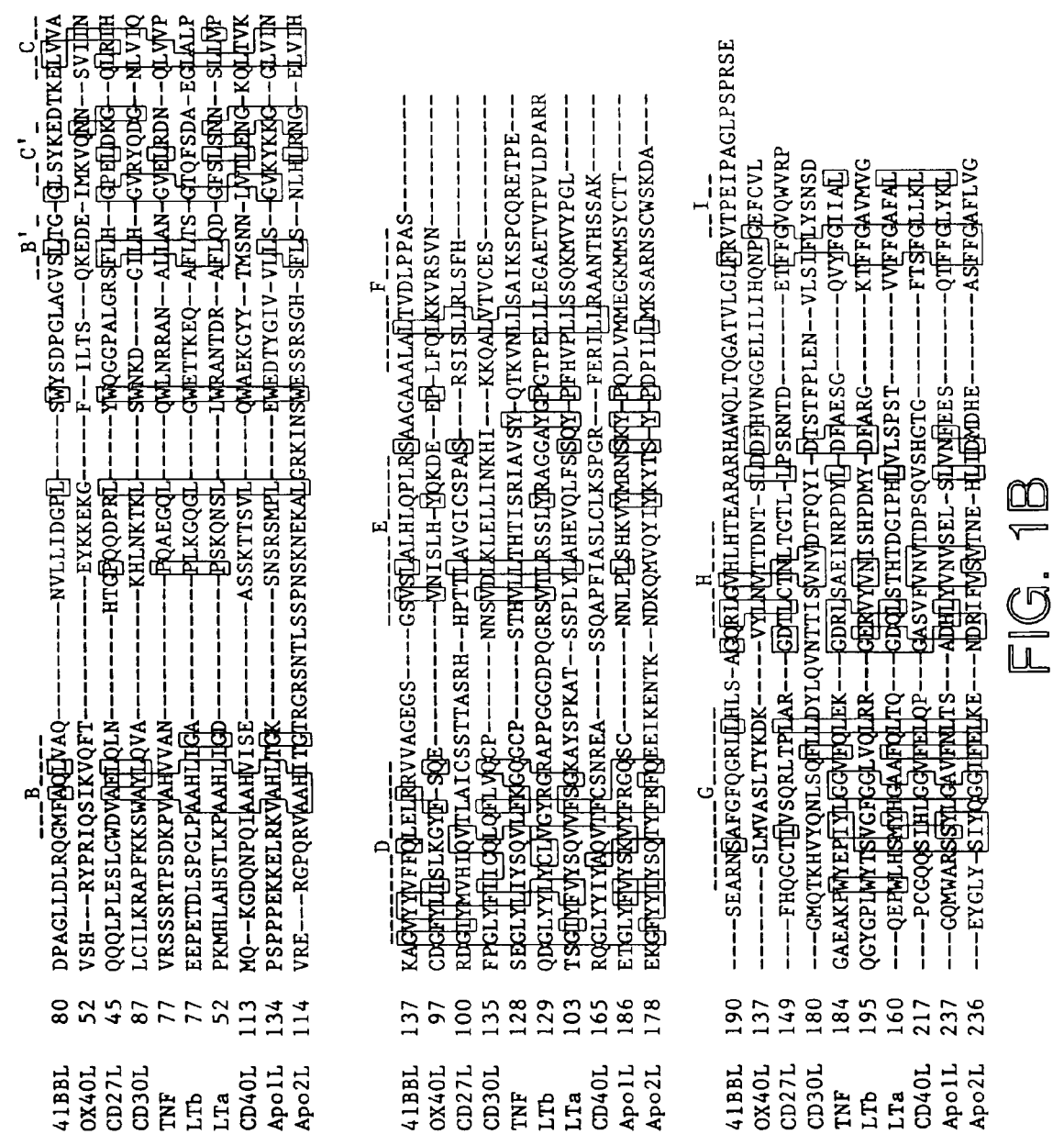
Figure 2A:
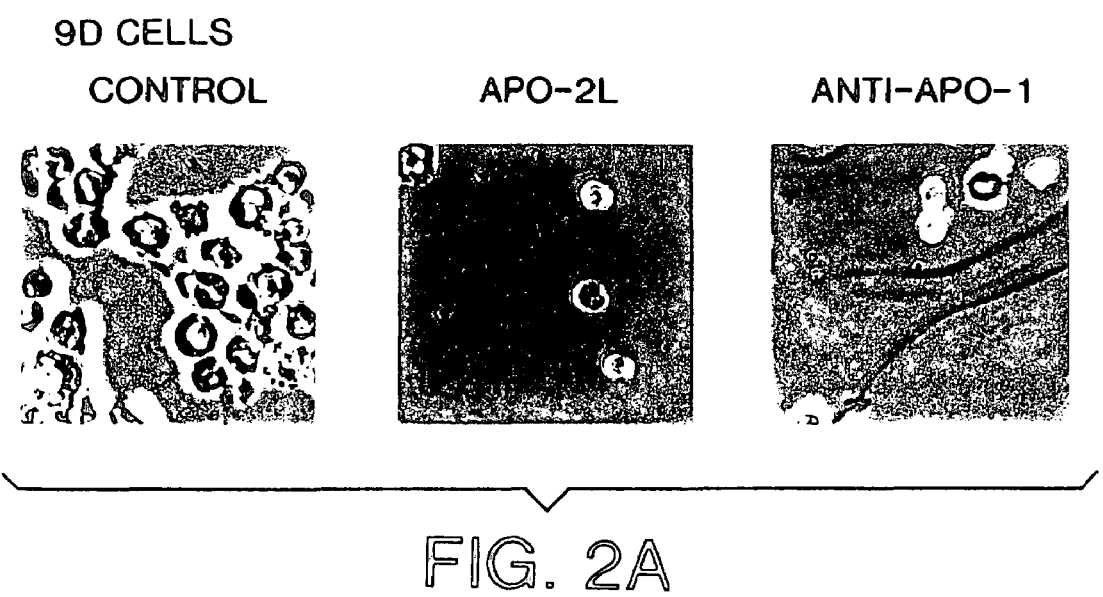

The terms "Apo-2 ligand" and "Apo-2L" are used herein to refer to a polypeptide sequence which includes amino acid residues 114–281, inclusive, residues 41–281, inclusive, residues 15–281, inclusive, or residues 1–281, inclusive, of the amino acid sequence shown in FIG. 1A, as well as biologically active deletional, insertional, or substitutional variants of the above sequences. In a preferred embodiment, the polypeptide sequence has at least residues 114–281 of FIG. 1A. In another preferred embodiment, the biologically active variants have at least about 80% sequence identity, more preferably at least about 90% sequence identity, and even more preferably, at least about 95% sequence identity with any one of the above sequences. The definition encompasses Apo-2 ligand isolated from an Apo-2 ligand source, such as from the human tissue types described herein (see Example 8) or from another source, or prepared by recombinant or synthetic methods. The present definition of Apo-2 ligand excludes known EST sequences, such as GenBank HHEA47M, T90422, R31020, H43566, H44565, H44567, H54628, H44772, H54629, T82085, and T10524.

The term "epitope tagged" when used herein refers to a chimeric polypeptide comprising Apo-2 ligand, or a portion thereof, fused to a "tag polypeptide". The tag polypeptide has enough residues to provide an epitope against which an antibody can be made, yet is short enough such that it does not interfere with activity of the Apo-2 ligand. The tag polypeptide preferably also is fairly unique so that the antibody does not substantially cross-react with other epitopes. Suitable tag polypeptides generally have at least six amino acid residues and usually between about 8 to about 50 amino acid residues (preferably, between about 10 to about 20 residues).

"Isolated," when used to describe the various proteins disclosed herein, means protein that has been identified and separated and/or recovered from a component of its natural environment. Contaminant components of its natural environment are materials that would typically interfere with diagnostic or therapeutic uses for the protein, and may include enzymes, hormones, and other proteinaceous or non-proteinaceous solutes. In preferred embodiments, the protein will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Isolated protein includes protein in situ within recombinant cells, since at least one component of the Apo-2 ligand natural environment will not be present. Ordinarily, however, isolated protein will be prepared by at least one purification step.

An "isolated" Apo-2 ligand nucleic acid molecule is a nucleic acid molecule that is identified and separated from at least one contaminant nucleic acid molecule with which it is ordinarily associated in the natural source of the Apo-2 ligand nucleic acid. An isolated Apo-2 ligand nucleic acid molecule is other than in the form or setting in which it is found in nature. Isolated Apo-2 ligand nucleic acid molecules therefore are distinguished from the Apo-2 ligand nucleic acid molecule as it exists in natural cells. However, an isolated Apo-2 ligand nucleic acid molecule includes Apo-2 ligand nucleic acid molecules contained in cells that ordinarily express Apo-2 ligand where, for example, the nucleic acid molecule is in a chromosomal location different from that of natural cells.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

The term "antibody" is used in the broadest sense and specifically covers single anti-Apo-2 ligand monoclonal antibodies (including agonist and antagonist antibodies) and anti-Apo-2 ligand antibody compositions with polyepitopic specificity.

The term "monoclonal antibody" as used herein refers to an antibody obtained from a population of substantially homogeneous antibodies, i.e., the individual antibodies comprising the population are identical except for possible naturally-occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen.

The monoclonal antibodies herein include hybrid and recombinant antibodies produced by splicing a variable (including hypervariable) domain of an anti-Apo-2 ligand antibody with a constant domain (e.g. "humanized" antibodies), or a light chain with a heavy chain, or a chain from one species with a chain from another species, or fusions with heterologous proteins, regardless of species of origin or immunoglobulin class or subclass designation, as well as antibody fragments (e.g., Fab, F(ab') 2, and Fv), so long as they exhibit the desired biological activity. See, e.g. U.S. Pat. No. 4,816,567 and Mage et al., in *Monoclonal Antibody Production Techniques and Applications*, pp. 79–97 (Marcel Dekker, Inc.: New York, 1987).

Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler and Milstein, *Nature,* 256:495 (1975), or may be made by recombinant DNA methods such as described in U.S. Pat. No. 4,816,567. The "monoclonal antibodies" may also be isolated from phage libraries generated using the techniques described in McCafferty et al., *Nature,* 348:552–554 (1990), for example.

"Humanized" forms of non-human (e.g. murine) antibodies are specific chimeric immunoglobulins, immunoglobulin chains, or fragments thereof (such as Fv, Fab, Fab', F(ab')$_2$ or other antigen-binding subsequences of antibodies) which contain minimal sequence derived from non-human immunoglobulin. For the most part, humanized antibodies are human immunoglobulins (recipient antibody) in which residues from a complementary determining region (CDR) of the recipient are replaced by residues from a CDR of a non-human species (donor antibody) such as mouse, rat, or rabbit having the desired specificity, affinity, and capacity. In some instances, Fv framework region (FR) residues of the human immunoglobulin are replaced by corresponding non-human residues. Furthermore, the humanized antibody may comprise residues which are found neither in the recipient antibody nor in the imported CDR or framework sequences. These modifications are made to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin.

"Biologically active" for the purposes herein means having the ability to induce or stimulate apoptosis in at least one type of mammalian cell in vivo or ex vivo.

The terms "apoptosis" and "apoptotic activity" are used in a broad sense and refer to the orderly or controlled form of cell death in mammals that is typically accompanied by one or more characteristic cell changes, including condensation of cytoplasm, loss of plasma membrane microvilli, segmentation of the nucleus, degradation of chromosomal DNA or loss of mitochondrial function. This activity can be determined and measured, for instance, by cell viability assays, FACS analysis or DNA electrophoresis.

The terms "cancer" and "cancerous" refer to or describe the physiological condition in mammals that is typically characterized by unregulated cell growth. Examples of cancer include but are not limited to, carcinoma, lymphoma, leukemia, blastoma, and sarcoma. More particular examples of such cancers include squamous cell carcinoma, small-cell lung cancer, non-small cell lung cancer, pancreatic cancer, glioblastoma multiforme, cervical cancer, stomach cancer, bladder cancer, hepatoma, breast cancer, colon carcinoma, and head and neck cancer. In a preferred embodiment, the cancer includes follicular lymphoma, carcinoma with p53 mutations, or hormone-dependent cancer such as breast cancer, prostate cancer, or ovarian cancer.

The terms "treating," "treatment," and "therapy" as used herein refer to curative therapy, prophylactic therapy, and preventative therapy.

The term "mammal" as used herein refers to any mammal classified as a mammal, including humans, cows, horses, dogs and cats. In a preferred embodiment of the invention, the mammal is a human.

II. Compositions and Methods of the Invention

The present invention provides a novel cytokine related to the TNF ligand family, the cytokine identified herein as "Apo-2 ligand." The predicted mature amino acid sequence of human Apo-2 ligand contains 281 amino acids, and has a calculated molecular weight of approximately 32.5 kDa and an isoelectric point of approximately 7.63. There is no apparent signal sequence at the N-terminus, although hydropathy analysis indicates the presence of a hydrophobic region between residues 15 and 40. The absence of a signal sequence and the presence of an internal hydrophobic region suggests that Apo-2 ligand is a type II transmembrane protein. A potential N-linked glycosylation site is located at residue 109 in the putative extracellular region. The putative cytoplasmic region comprises amino acid residues 1–14, the transmembrane region comprises amino acid residues 15–40 and the extracellular region comprises amino acid residues 41–281, shown in FIG. 1A. An Apo-2 ligand polypeptide comprising amino acid residues 114–281 of the extracellular region, shown in FIG. 1A, is also described in the Examples below.

A. Preparation of Apo-2 Ligand

The description below relates primarily to production of Apo-2 ligand by culturing cells transformed or transfected with a vector containing Apo-2 ligand nucleic acid and recovering the polypeptide from the cell culture. It is of course, contemplated that alternative methods, which are well known in the art, may be employed to prepare Apo-2 ligand.

1. Isolation of DNA Encoding Apo-2 Ligand

The DNA encoding Apo-2 ligand may be obtained from any cDNA library prepared from tissue believed to possess the Apo-2 ligand mRNA and to express it at a detectable level. Accordingly, human Apo-2 ligand DNA can be conveniently obtained from a cDNA library prepared from human tissues, such as the bacteriophage library of human placental cDNA described in Example 1. The Apo-2 ligand-encoding gene may also be obtained from a genomic library or by oligonucleotide synthesis.

Libraries can be screened with probes (such as antibodies to the Apo-2 ligand or oligonucleotides of at least about 20–80 bases) designed to identify the gene of interest or the protein encoded by it. Examples of oligonucleotide probes are provided in Example 1. Screening the cDNA or genomic library with the selected probe may be conducted using standard procedures, such as described in Sambrook et al., *Molecular Cloning: A Laboratory Manual* (New York: Cold Spring Harbor Laboratory Press, 1989). An alternative means to isolate the gene encoding Apo-2 ligand is to use PCR methodology [Sambrook et al., supra; Dieffenbach et al., *PCR Primer: A Laboratory Manual* (Cold Spring Harbor Laboratory Press, 1995)].

A preferred method of screening employs selected oligonucleotide sequences to screen cDNA libraries from various human tissues. Example 1 below describes techniques for screening a cDNA library with two different oligonucleotide probes. The oligonucleotide sequences selected as probes should be of sufficient length and sufficiently unambiguous that false positives are minimized. The oligonucleotide is preferably labeled such that it can be detected upon hybridization to DNA in the library being screened. Methods of labeling are well known in the art, and include the use of radiolabels like $^{32}$P-labeled ATP, biotinylation or enzyme labeling.

Nucleic acid having all the protein coding sequence may be obtained by screening selected cDNA or genomic libraries using the deduced amino acid sequence disclosed herein for the first time, and, if necessary, using conventional primer extension procedures as described in Sambrook et al., supra, to detect precursors and processing intermediates of mRNA that may not have been reverse-transcribed into cDNA.

Amino acid sequence variants of Apo-2 ligand can be prepared by introducing appropriate nucleotide changes into the Apo-2 ligand DNA, or by synthesis of the desired Apo-2 ligand polypeptide. Such variants represent insertions, substitutions, and/or deletions of residues within or at one or both of the ends of the intracellular region, the transmembrane region, or the extracellular region, or of the amino acid sequence shown for the full-length Apo-2 ligand in FIG. 1A. Any combination of insertion, substitution, and/or deletion can be made to arrive at the final construct, provided that the final construct possesses the desired apoptotic activity as defined herein. In a preferred embodiment, the variants have at least about 80% sequence identity, more preferably, at least about 90% sequence identity, and even more preferably, at least about 95% sequence identity with the sequences identified herein for the intracellular, transmembrane, or extracellular regions of Apo-2 ligand, or the full-length sequence for Apo-2 ligand. The amino acid changes also may alter post-translational processes of the Apo-2 ligand, such as changing the number or position of glycosylation sites or altering the membrane anchoring characteristics.

Variations in the native sequence as described above can be made using any of the techniques and guidelines for conservative and non-conservative mutations set forth in U.S. Pat. No. 5,364,934. These include oligonucleotide-mediated (site-directed) mutagenesis, alanine scanning, and PCR mutagenesis.

2. Insertion of Nucleic Acid into A Replicable Vector

The nucleic acid (e.g., cDNA or genomic DNA) encoding native or variant Apo-2 ligand may be inserted into a replicable vector for further cloning (amplification of the DNA) or for expression. Various vectors are publicly available. The vector components generally include, but are not limited to, one or more of the following: a signal sequence, an origin of replication, one or more marker genes, an enhancer element, a promoter, and a transcription termination sequence, each of which is described below.

(i) Signal Sequence Component

The Apo-2 ligand may be produced recombinantly not only directly, but also as a fusion polypeptide with a heterologous polypeptide, which may be a signal sequence or other polypeptide having a specific cleavage site at the N-terminus of the mature protein or polypeptide. In general, the signal sequence may be a component of the vector, or it may be a part of the Apo-2 ligand DNA that is inserted into the vector. The heterologous signal sequence selected preferably is one that is recognized and processed (i.e., cleaved by a signal peptidase) by the host cell. The signal sequence may be a prokaryotic signal sequence selected, for example, from the group of the alkaline phosphatase, penicillinase, 1 pp, or heat-stable enterotoxin II leaders. For yeast secretion the signal sequence may be, e.g., the yeast invertase leader, alpha factor leader (including *Saccharomyces* and *Kluyveromyces* α-factor leaders, the latter described in U.S. Pat. No. 5,010,182), or acid phosphatase leader, the *C. albicans* glucoamylase leader (EP 362,179 published 4 Apr. 1990), or the signal described in WO 90/13646 published 15 Nov. 1990. In mammalian cell expression the native Apo-2 ligand presequence that normally directs insertion of Apo-2 ligand in the cell membrane of human cells in vivo is satisfactory, although other mammalian signal sequences may be used to direct secretion of the protein, such as signal sequences from secreted polypeptides of the same or related species, as well as viral secretory leaders, for example, the herpes simplex glycoprotein D signal.

The DNA for such precursor region is preferably ligated in reading frame to DNA encoding Apo-2 ligand.

(ii) Origin of Replication Component

Both expression and cloning vectors contain a nucleic acid sequence that enables the vector to replicate in one or more selected host cells. Generally, in cloning vectors this sequence I—S is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the $2\mu$ plasmid origin is suitable for yeast, and various viral origins (SV40, polyoma, adenovirus, VSV or BPV) are useful for cloning vectors in mammalian cells. Generally, the origin of replication component is not needed for mammalian expression vectors (the SV40 origin may typically be used because it contains the early promoter).

Most expression vectors are "shuttle" vectors, i.e., they are capable of replication in at least one class of organisms but can be transfected into another organism for expression. For example, a vector is cloned in *E. coli* and then the same vector is transfected into yeast or mammalian cells for expression even though it is not capable of replicating independently of the host cell chromosome.

DNA may also be amplified by insertion into the host genome. This is readily accomplished using *Bacillus* species as hosts, for example, by including in the vector a DNA sequence that is complementary to a sequence found in *Bacillus* genomic DNA. Transfection of *Bacillus* with this vector results in homologous recombination with the genome and insertion of Apo-2 ligand DNA. However, the recovery of genomic DNA encoding Apo-2 ligand is more complex than that of an exogenously replicated vector because restriction enzyme digestion is required to excise the Apo-2 ligand DNA.

(iii) Selection Gene Component

Expression and cloning vectors typically contain a selection gene, also termed a selectable marker. This gene encodes a protein necessary for the survival or growth of transformed host cells grown in a selective culture medium. Host cells not transformed with the vector containing the selection gene will not survive in the culture medium. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin [Southern et al., *J. Molec. Appl. Genet.*, 1:327 (1982)], mycophenolic acid (Mulligan et al., *Science*, 209: 1422 (1980) or hygromycin [Sugden et al., *Mol. Cell. Biol.*, 5:410–413 (1985)]. The three examples given above employ bacterial genes under eukaryotic control to convey resistance to the appropriate drug G418 or neomycin (geneticin), xgpt (mycophenolic acid), or hygromycin, respectively.

Another example of suitable selectable markers for mammalian cells are those that enable the identification of cells competent to take up the Apo-2 ligand nucleic acid, such as DHFR or thymidine kinase. The mammalian cell transformants are placed under selection pressure that only the transformants are uniquely adapted to survive by virtue of having taken up the marker. Selection pressure is imposed by culturing the transformants under conditions in which the concentration of selection agent in the medium is successively changed, thereby leading to amplification of both the selection gene and the DNA that encodes Apo-2 ligand. Amplification is the process by which genes in greater demand for the production of a protein critical for growth are reiterated in tandem within the chromosomes of successive generations of recombinant cells. Increased quantities of Apo-2 ligand are synthesized from the amplified DNA. Other examples of amplifiable genes include metallothionein-I and -II, adenosine deaminase, and ornithine decarboxylase.

Cells transformed with the DHFR selection gene may first be identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity, prepared and propagated as described by Urlaub et al., *Proc. Natl. Acad. Sci. USA,* 77:4216 (1980). The transformed cells are then exposed to increased levels of methotrexate. This leads to the synthesis of multiple copies of the DHFR gene, and, concomitantly, multiple copies of other DNA comprising the expression vectors, such as the DNA encoding Apo-2 ligand. This amplification technique can be used with any otherwise suitable host, e.g., ATCC No. CCL61 CHO-K1, notwithstanding the presence of endogenous DHFR if, for example, a mutant DHFR gene that is highly resistant to Mtx is employed (EP 117,060).

Alternatively, host cells (particularly wild-type hosts that contain endogenous DHFR) transformed or co-transformed with DNA sequences encoding Apo-2 ligand, wild-type DHFR protein, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

A suitable selection gene for use in yeast is the trp1 gene present in the yeast plasmid YRp7 [Stinchcomb et al., *Nature,* 282:39 (1979); Kingsman et al., *Gene,* 7:141 (1979); Tschemper et al., *Gene,* 10:157 (1980)]. The trp1 gene provides a selection marker for a mutant strain of yeast lacking the ability to grow in tryptophan, for example, ATCC No. 44076 or PEP4-1 [Jones, *Genetics,* 85:12 (1977)]. The presence of the trp1 lesion in the yeast host cell genome then provides an effective environment for detecting transformation by growth in the absence of tryptophan. Similarly, Leu2-deficient yeast strains (ATCC 20,622 or 38,626) are complemented by known plasmids bearing the Leu2 gene.

In addition, vectors derived from the 1.6 $\mu$m circular plasmid pKD1 can be used for transformation of *Kluyveromyces* yeasts [Bianchi et al., *Curr. Genet.,* 12:185 (1987)]. More recently, an expression system for large-scale production of recombinant calf chymosin was reported for *K. lactis* [Van den Berg, *Bio/Technology,* 8:135 (1990)]. Stable multicopy expression vectors for secretion of mature recombinant human serum albumin by industrial strains of *Kluyveromyces* have also been disclosed [Fleer et al., *Bio/Technology,* 9:968–975 (1991)].

(iv) Promoter Component

Expression and cloning vectors usually contain a promoter that is recognized by the host organism and is operably linked to the Apo-2 ligand nucleic acid sequence. Promoters are untranslated sequences located upstream (5') to the start codon of a structural gene (generally within about 100 to 1000 bp) that control the transcription and translation of particular nucleic acid sequence, such as the Apo-2 ligand nucleic acid sequence, to which they are operably linked. Such promoters typically fall into two classes, inducible and constitutive. Inducible promoters are promoters that initiate increased levels of transcription from DNA under their control in response to some change in culture conditions, e.g., the presence or absence of a nutrient or a change in temperature. At this time a large number of promoters recognized by a variety of potential host cells are well known. These promoters are operably linked to Apo-2 ligand encoding DNA by removing the promoter from the source DNA by restriction enzyme digestion and inserting the isolated promoter sequence into the vector. Both the native Apo-2 ligand promoter sequence and many heterologous promoters may be used to direct amplification and/or expression of the Apo-2 ligand DNA.

Promoters suitable for use with prokaryotic hosts include the $\beta$-lactamase and lactose promoter systems [Chang et al., *Nature,* 275:615 (1978); Goeddel et al., *Nature,* 281:544 (1979)], alkaline phosphatase, a tryptophan (trp) promoter system [Goeddel, *Nucleic Acids Res.,* 8:4057 (1980); EP 36,776], and hybrid promoters such as the tac promoter [deBoer et al., *Proc. Natl. Acad. Sci. USA,* 80:21–25 (1983)]. However, other known bacterial promoters are suitable. Their nucleotide sequences have been published, thereby enabling a skilled worker operably to ligate them to DNA encoding Apo-2 ligand [Siebenlist et al., *Cell,* 20:269 (1980)] using linkers or adaptors to supply any required restriction sites. Promoters for use in bacterial systems also will contain a Shine-Dalgarno (S.D.) sequence operably linked to the DNA encoding Apo-2 ligand.

Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CXCAAT region where X may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

Examples of suitable promoting sequences for use with yeast hosts include the promoters for 3-phosphoglycerate kinase [Hitzeman et al., *J. Biol. Chem.,* 255:2073 (1980)] or other glycolytic enzymes [Hess et al., *J. Adv. Enzyme Req.,* 7:149 (1968); Holland, *Biochemistry,* 17:4900 (1978)], such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657. Yeast enhancers also are advantageously used with yeast promoters.

Apo-2 ligand transcription from vectors in mammalian host cells is controlled, for example, by promoters obtained from the genomes of viruses such as polyoma virus, fowlpox virus (UK 2,211,504 published 5 Jul. 1989), adenovirus (such as Adenovirus 2), bovine papilloma virus, avian sarcoma virus, cytomegalovirus, a retrovirus, hepatitis-B virus and most preferably Simian Virus 40 (SV40), from heterologous mammalian promoters, e.g., the actin promoter or an immunoglobulin promoter, from heat-shock promoters, and from the promoter normally associated with the Apo-2 ligand sequence, provided such promoters are compatible with the host cell systems.

The early and late promoters of the SV40 virus are conveniently obtained as an SV40 restriction fragment that also contains the SV40 viral origin of replication [Fiers et al., *Nature,* 273:113 (1978); Mulligan and Berg, *Science,* 209:1422–1427 (1980); Pavlakis et al., *Proc. Natl. Acad. Sci. USA,* 78:7398–7402 (1981)]. The immediate early promoter of the human cytomegalovirus is conveniently obtained as a HindIII E restriction fragment [Greenaway et al., *Gene,* 18:355–360 (1982)]. A system for expressing DNA in mammalian hosts using the bovine papilloma virus as a vector is disclosed in U.S. Pat. No. 4,419,446. A modification of this system is described in U.S. Pat. No. 4,601,978 [See also Gray et al., *Nature,* 295:503–508 (1982) on expressing cDNA encoding immune interferon in monkey cells; Reyes et al., *Nature,* 297:598–601 (1982) on expression of human β-interferon cDNA in mouse cells under the control of a thymidine kinase promoter from herpes simplex virus; Canaani and Berg, *Proc. Natl. Acad. Sci. USA* 79:5166–5170 (1982) on expression of the human interferon β1 gene in cultured mouse and rabbit cells; and Gorman et al., *Proc. Natl. Acad. Sci. USA,* 79:6777–6781 (1982) on expression of bacterial CAT sequences in CV-1 monkey kidney cells, chicken embryo fibroblasts, Chinese hamster ovary cells, HeLa cells, and mouse NIH-3T3 cells using the Rous sarcoma virus long terminal repeat as a promoter].

(v) Enhancer Element Component

Transcription of a DNA encoding the Apo-2 ligand of this invention by higher eukaryotes may be increased by inserting an enhancer sequence into the vector. Enhancers are cis-acting elements of DNA, usually about from 10 to 300 bp, that act on a promoter to increase its transcription. Enhancers are relatively orientation and position independent, having been found 5' [Laimins et al., *Proc. Natl. Acad. Sci. USA,* 78:993 (1981]) and 3' [Lusky et al., *Mol. Cell Bio.,* 3:1108 (1983]) to the transcription unit, within an intron [Banerji et al., *Cell,* 33:729 (1983)], as well as within the coding sequence itself [Osborne et al., *Mol. Cell Bio.,* 4:1293 (1984)]. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100–270), the cytomegalovirus early promoter enhancer, the polyoma enhancer on the late side of the replication origin, and adenovirus enhancers. See also Yaniv, *Nature,* 297: 17–18 (1982) on enhancing elements for activation of eukaryotic promoters. The enhancer may be spliced into the vector at a position 5' or 3' to the Apo-2 ligand-encoding sequence, but is preferably located at a site 5' from the promoter.

(vi) Transcription Termination Component

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding Apo-2 ligand.

(vii) Construction and Analysis of Vectors

Construction of suitable vectors containing one or more of the above-listed components employs standard ligation techniques. Isolated plasmids or DNA fragments are cleaved, tailored, and re-ligated in the form desired to generate the plasmids required.

For analysis to confirm correct sequences in plasmids constructed, the ligation mixtures can be used to transform *E. coli* K12 strain 294 (ATCC 31,446) and successful transformants selected by ampicillin or tetracycline resistance where appropriate. Plasmids from the transformants are prepared, analyzed by restriction endonuclease digestion, and/or sequenced by the method of Messing et al., *Nucleic Acids Res.,* 9:309 (1981) or by the method of Maxam et al., *Methods in Enzymology,* 65:499 (1980).

(viii) Transient Expression Vectors

Expression vectors that provide for the transient expression in mammalian cells of DNA encoding Apo-2 ligand may be employed. In general, transient expression involves the use of an expression vector that is able to replicate efficiently in a host cell, such that the host cell accumulates many copies of the expression vector and, in turn, synthesizes high levels of a desired polypeptide encoded by the expression vector [Sambrook et al., supra]. Transient expression systems, comprising a suitable expression vector and a host cell, allow for the convenient positive identification of polypeptides encoded by cloned DNAs, as well as for the rapid screening of such polypeptides for desired biological or physiological properties. Thus, transient expression systems are particularly useful in the invention for purposes of identifying analogs and variants of Apo-2 ligand that are biologically active Apo-2 ligand.

(ix) Suitable Exemplary Vertebrate Cell Vectors

Other methods, vectors, and host cells suitable for adaptation to the synthesis of Apo-2 ligand in recombinant vertebrate cell culture are described in Gething et al., *Nature,* 293:620–625 (1981); Mantei et al., *Nature,* 281:40–46 (1979);. EP 117,060; and EP 117,058. A particularly useful plasmid for mammalian cell culture expression of Apo-2 ligand is PRK5 [EP 307,247; also described in Example 1] or pSVI6B [WO 91/08291 published 13 Jun. 1991].

3. Selection and Transformation of Host Cells

Suitable host cells for cloning or expressing the DNA in the vectors herein are the prokaryote, yeast, or higher eukaryote cells described above. Suitable prokaryotes for this purpose include but are not limited to eubacteria, such as Gram-negative or Gram-positive organisms, for example, Enterobacteriaceae such as *Escherichia,* e.g., *E. coli, Enterobacter, Erwinia, Klebsiella, Proteus, Salmonella,* e.g., *Salmonella typhimurium, Serratia,* e.g., *Serratia marcescans,* and *Shigella,* as well as Bacilli such as *B. subtilis* and *B. licheniformis* (e.g., *B. licheniformis* 41P disclosed in DD 266,710 published 12 Apr. 1989), *Pseudomonas* such as *P. aeruginosa,* and *Streptomyces.* Preferably, the host cell should secrete minimal amounts of proteolytic enzymes.

In addition to prokaryotes, eukaryotic microbes such as filamentous fungi or yeast are suitable cloning or expression hosts for Apo-2 ligand-encoding vectors. *Saccharomyces cerevisiae,* or common baker's yeast, is the most commonly used among lower eukaryotic host microorganisms. However, a number of other genera, species, and strains are commonly available and useful herein.

Suitable host cells for the expression of glycosylated Apo-2 ligand are derived from multicellular organisms. Such host cells are capable of complex processing and glycosylation activities. In principle, any higher eukaryotic cell culture is workable, whether from vertebrate or invertebrate culture. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified [See, e.g., Luckow et al., *Bio/Technology,* 6:47–55 (1988); Miller et al., in *Genetic Engineering,* Setlow et al., eds., Vol. 8 (Plenum Publishing, 1986), pp. 277–279; and Maeda et al., *Nature,* 315:592–594 (1985)]. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* ("Sf9") cells, described in Example 2.

Plant cell cultures of cotton, corn, potato, soybean, petunia, tomato, and tobacco can be utilized as hosts. Typically, plant cells are transfected by incubation with certain strains of the bacterium *Agrobacterium tumefaciens*, which has been previously manipulated to contain the Apo-2 ligand-encoding DNA. During incubation of the plant cell culture with *A. tumefaciens*, the DNA encoding the Apo-2 ligand is transferred to the plant cell host such that it is transfected, and will, under appropriate conditions, express the Apo-2 ligand-encoding DNA. In addition, regulatory and signal sequences compatible with plant cells are available, such as the nopaline synthase promoter and polyadenylation signal sequences [Depicker et al., *J. Mol. Appl. Gen.*, 1:561 (1982)]. In addition, DNA segments isolated from the upstream region of the T-DNA 780 gene are capable of activating or increasing transcription levels of plant-expressible genes in recombinant DNA-containing plant tissue [EP 321,196 published 21 Jun. 1989].

Propagation of vertebrate cells in culture (tissue culture) is also well known in the art [See, e.g., *Tissue Culture*, Academic Press, Kruse and Patterson, editors (1973)]. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., *J. Gen Virol.*, 36:59 (1977)); baby hamster kidney cells (BHK, ATCC CCL 10); Chinese hamster ovary cells/-DHFR (CHO, Urlaub and Chasin, *Proc. Natl. Acad. Sci. USA*, 77:4216 (1980)); mouse sertoli cells (TM4, Mather, *Biol. Reprod.*, 23:243–251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y. Acad. Sci.*, 383:44–68 (1982)); MRC 5 cells; and FS4 cells.

Host cells are transfected and preferably transformed with the above-described expression or cloning vectors for Apo-2 ligand production and cultured in conventional nutrient media modified as appropriate for inducing promoters, selecting transformants, or amplifying the genes encoding the desired sequences.

Transfection refers to the taking up of an expression vector by a host cell whether or not any coding sequences are in fact expressed. Numerous methods of transfection are known to the ordinarily skilled artisan, for example, $CaPO_4$ and electroporation. Successful transfection is generally recognized when any indication of the operation of this vector occurs within the host cell.

Transformation means introducing DNA into an organism so that the DNA is replicable, either as an extrachromosomal element or by chromosomal integrant. Depending on the host cell used, transformation is done using standard techniques appropriate to such cells. The calcium treatment employing calcium chloride, as described in Sambrook et al., supra, or electroporation is generally used for prokaryotes or other cells that contain substantial cell-wall barriers. Infection with *Agrobacterium tumefaciens* is used for transformation of certain plant cells, as described by Shaw et al., *Gene*, 23:315 (1983) and WO 89/05859 published 29 Jun. 1989. In addition, plants may be transfected using ultrasound treatment as described in WO 91/00358 published 10 Jan. 1991.

For mammalian cells without such cell walls, the calcium phosphate precipitation method of Graham and van der Eb, *Virology*, 52:456–457 (1978) is preferred. General aspects of mammalian cell host system transformations have been described in U.S. Pat. No. 4,399,216. Transformations into yeast are typically carried out according to the method of Van Solingen et al., *J. Bact.*, 130:946 (1977) and Hsiao et al., *Proc. Natl. Acad. Sci.* (USA), 76:3829 (1979). However, other methods for introducing DNA into cells, such as by nuclear microinjection, electroporation, bacterial protoplast fusion with intact cells, or polycations, e.g., polybrene, polyornithine, may also be used. For various techniques for transforming mammalian cells, see Keown et al., *Methods in Enzymology*, 185:527–537 (1990) and Mansour et al., *Nature*, 336:348–352 (1988).

4. Culturing the Host Cells

Prokaryotic cells used to produce Apo-2 ligand may be cultured in suitable media as described generally in Sambrook et al., supra.

The mammalian host cells used to produce Apo-2 ligand may be cultured in a variety of media. Examples of commercially available media include Ham's F10 (Sigma), Minimal Essential Medium ("MEM", Sigma), RPMI-1640 (Sigma), and Dulbecco's Modified Eagle's Medium ("DMEM", Sigma). Any such media may be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics (such as Gentamycin™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

In general, principles, protocols, and practical techniques for maximizing the productivity of mammalian cell cultures can be found in *Mammalian Cell Biotechnology: a Practical Approach*, M. Butler, ed. (IRL Press, 1991).

The host cells referred to in this disclosure encompass cells in culture as well as cells that are within a host animal.

5. Detecting Gene Amplification/Expression

Gene amplification and/or expression may be measured in a sample directly, for example, by conventional Southern blotting, Northern blotting to quantitate the transcription of mRNA [Thomas, *Proc. Natl. Acad. Sci. USA*, 77:5201–5205 (1980)], dot blotting (DNA analysis), or in situ hybridization, using an appropriately labeled probe, based on the sequences provided herein. Various labels may be employed, most commonly radioisotopes, and particularly $^{32}P$. However, other techniques may also be employed, such as using biotin-modified nucleotides for introduction into a polynucleotide. The biotin then serves as the site for binding to avidin or antibodies, which may be labeled with a wide variety of labels, such as radionucleotides, fluorescers or enzymes. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of cells or tissue sections and assay of cell culture or body fluids, to quantitate directly the expression of gene product. With immunohistochemical staining techniques, a cell sample is prepared, typically by dehydration and fixation, followed by reaction with labeled antibodies specific for the gene product coupled, where the labels are usually visually detectable, such as enzymatic labels, fluorescent labels, luminescent labels, and the like.

Antibodies useful for immunohistochemical staining and/or assay of sample fluids may be either monoclonal or polyclonal, and may be prepared in any mammal. Conveniently, the antibodies may be prepared against a native Apo-2 ligand polypeptide or against a synthetic peptide based on the DNA sequences provided herein or against exogenous sequence fused to Apo-2 ligand DNA and encoding a specific antibody epitope.

6. Purification of Apo-2 Ligand Polypeptide

Apo-2 ligand preferably is recovered from the culture medium as a secreted polypeptide, although it also may be recovered from host cell lysates when directly produced without a secretory signal. If the Apo-2 ligand is membrane-bound, it can be released from the membrane using a suitable detergent solution (e.g. Triton-X 100) or its extracellular region may be released by enzymatic cleavage.

When Apo-2 ligand is produced in a recombinant cell other than one of human origin, the Apo-2 ligand is free of proteins or polypeptides of human origin. However, it is usually necessary to purify Apo-2 ligand from recombinant cell proteins or polypeptides to obtain preparations that are substantially homogeneous as to Apo-2 ligand. As a first step, the culture medium or lysate may be centrifuged to remove particulate cell debris. Apo-2 ligand thereafter is purified from contaminant soluble proteins and polypeptides, with the following procedures being exemplary of suitable purification procedures: by fractionation on an ion-exchange column; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex G-75; and protein A Sepharose columns to remove contaminants such as IgG.

In a preferred embodiment, the Apo-2 ligand can be isolated by affinity chromatography, as described in Example 3.

Apo-2 ligand variants in which residues have been deleted, inserted, or substituted are recovered in the same fashion as native Apo-2 ligand, taking account of any substantial changes in properties occasioned by the variation. For example, preparation of an Apo-2 ligand fusion with another protein or polypeptide, e.g., a bacterial or viral antigen, facilitates purification; an immunoaffinity column containing antibody to the antigen can be used to adsorb the fusion polypeptide. In a preferred embodiment, an extracellular sequence of Apo-2 ligand is fused to a $His_1$ peptide and purified by $Ni^{2+}$-chelate affinity chromatography.

A protease inhibitor such as phenyl methyl sulfonyl fluoride (PMSF) also may be useful to inhibit proteolytic degradation during purification, and antibiotics may be included to prevent the growth of adventitious contaminants. One skilled in the art will appreciate that purification methods suitable for native Apo-2 ligand may require modification to account for changes in the character of Apo-2 ligand or its variants upon expression in recombinant cell culture.

7. Covalent Modifications of Apo-2 Ligand Polypeptides

Covalent modifications of Apo-2 ligand are included within the scope of this invention. Both native Apo-2 ligand and amino acid sequence variants of the Apo-2 ligand may be covalently modified. One type of covalent modification of the Apo-2 ligand is introduced into the molecule by reacting targeted amino acid residues of the Apo-2 ligand with an organic derivatizing agent that is capable of reacting with selected side chains or the N- or C-terminal residues of the Apo-2 ligand.

Derivatization with bifunctional agents is useful for crosslinking Apo-2 ligand to a water-insoluble support matrix or surface for use in the method for purifying anti-Apo-2 ligand antibodies, and vice-versa. Commonly used crosslinking agents include, e.g., 1,1-bis(diazoacetyl)-2-phenylethane, glutaraldehyde, N-hydroxysuccinimide esters, for example, esters with 4-azido-salicylic acid, homobifunctional imidoesters, including disuccinimidyl esters such as 3,3'-dithiobis(succinimidyl-propionate), and bifunctional maleimides such as bis-N-maleimido-1,8-octane. Derivatizing agents such as methyl-3-[(p-azidophenyl)-dithio]propioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 are employed for protein immobilization.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the α-amino groups of lysine, arginine, and histidine side chains [T. E. Creighton, *Proteins: Structure and Molecular Properties*, W.H. Freeman & Co., San Francisco, pp. 79–86 (1983)], acetylation of the N-terminal amine, and amidation of any C-terminal carboxyl group. The modified forms of the residues fall within the scope of the present invention.

Another type of covalent modification of the Apo-2 ligand polypeptide included within the scope of this invention comprises altering the native glycosylation pattern of the polypeptide. "Altering the native glycosylation pattern" is intended for purposes herein to mean deleting one or more carbohydrate moieties found in native Apo-2 ligand, and/or adding one or more glycosylation sites that are not present in the native Apo-2 ligand.

Glycosylation of polypeptides is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxylamino acid, most commonly serine or threonine, although 5-hydroxyproline or 5-hydroxylysine may also be used.

Addition of glycosylation sites to the Apo-2 ligand polypeptide may be accomplished by altering the amino acid sequence such that it contains one or more of the above-described tripeptide sequences (for N-linked glycosylation sites). The alteration may also be made by the addition of, or substitution by, one or more serine or threonine residues to the native Apo-2 ligand sequence (for O-linked glycosylation sites). The Apo-2 ligand amino acid sequence may optionally be altered through changes at the DNA level, particularly by mutating the DNA encoding the Apo-2 ligand polypeptide at preselected bases such that codons are generated that will translate into the desired amino acids. The DNA mutation(s) may be made using methods described above and in U.S. Pat. No. 5,364,934, supra.

Another means of increasing the number of carbohydrate moieties on the Apo-2 ligand polypeptide is by chemical or enzymatic coupling of glycosides to the polypeptide. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. These methods are described in WO 87/05330 published 11 Sep. 1987, and in Aplin and Wriston, *CRC Crit. Rev. Biochem.,* pp. 259–306 (1981).

Removal of carbohydrate moieties present on the Apo-2 ligand polypeptide may be accomplished chemically or enzymatically. For instance, chemical deglycosylation by exposing the polypeptide to the compound trifluoromethanesulfonic acid, or an equivalent compound can result in the cleavage of most or all sugars except the linking sugar (N-acetylglucosamine or N-acetylgalactosamine), while leaving the polypeptide intact. Chemical deglycosylation is described by Hakimuddin, et al., *Arch. Biochem. Biophys.,* 259:52 (1987) and by Edge et al., *Anal. Biochem.,* 118:131 (1981). Enzymatic cleavage of carbohydrate moieties on polypeptides can be achieved by the use of a variety of endo- and exo-glycosidases as described by Thotakura et al., *Meth. Enzymol.,* 138:350 (1987).

Glycosylation at potential glycosylation sites may be prevented by the use of the compound tunicamycin as described by Duskin et al., *J. Biol. Chem.,* 257:3105 (1982). Tunicamycin blocks the formation of protein-N-glycoside linkages.

Another type of covalent modification of Apo-2 ligand comprises linking the Apo-2 ligand polypeptide to one of a variety of nonproteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192 or 4,179,337.

8. Epitope-Tagged Apo-2 Ligand

The present invention also provides chimeric polypeptides comprising Apo-2 ligand fused to another, heterologous polypeptide. In one embodiment, the chimeric polypeptide comprises a fusion of the Apo-2 ligand with a tag polypeptide which provides an epitope to which an anti-tag antibody can selectively bind. The epitope tag is generally placed at the amino- or carboxyl-terminus of the Apo-2 ligand. The presence of such epitope-tagged forms of the Apo-2 ligand can be detected using an antibody against the tag polypeptide. Also, provision of the epitope tag enables the Apo-2 ligand to be readily purified by affinity purification using an anti-tag antibody or another type of affinity matrix that binds to the epitope tag.

Various tag polypeptides and their respective antibodies are well known in the art. Examples include the flu HA tag polypeptide and its antibody 12CA5 [Field et al., *Mol. Cell. Biol.,* 8:2159–2165 (1988)]; the c-myc tag and the 8F9, 3C7, 6E10, G4, B7 and 9E10 antibodies thereto [Evan et al., *Molecular and Cellular Biology,* 5:3610–3616 (1985)]; and the Herpes Simplex virus glycoprotein D (gD) tag and its antibody [Paborsky et al., *Protein Engineering,* 3(6):547–553 (1990)]. Other tag polypeptides include the Flag-peptide [Hopp et al., *BioTechnology,* 6:1204–1210 (1988)]; the KT3 epitope peptide [Martin et al., *Science,* 255:192—194 (1992)]; an α-tubulin epitope peptide [Skinner et al., *J. Biol. Chem.,* 266:15163–15166 (1991)]; and the T7 gene 10 protein peptide tag [Lutz-Freyermuth et al., *Proc. Natl. Acad. Sci. USA,* 87:6393–6397 (1990)]. Once the tag polypeptide has been selected, an antibody thereto can be generated using the techniques disclosed herein.

Generally, epitope-tagged Apo-2 ligand may be constructed and produced according to the methods described above for native and variant Apo-2 ligand. Apo-2 ligand-tag polypeptide fusions are preferably constructed by fusing the cDNA sequence encoding the Apo-2 ligand portion in-frame to the tag polypeptide DNA sequence and expressing the resultant DNA fusion construct in appropriate host cells. Ordinarily, when preparing the Apo-2 ligand-tag polypeptide chimeras of the present invention, nucleic acid encoding the Apo-2 ligand will be fused at its 3' end to nucleic acid encoding the N-terminus of the tag polypeptide, however 5' fusions are also possible. Examples of epitope-tagged Apo-2 ligand are described in further detail in Example 2 below.

Epitope-tagged Apo-2 ligand can be purified by affinity chromatography using the anti-tag antibody. The matrix to which the affinity antibody is attached may include, for instance, agarose, controlled pore glass or poly(styrenedivinyl)benzene). The epitope-tagged Apo-2 ligand can then be eluted from the affinity column using techniques known in the art.

B. Therapeutic Uses for Apo-2 Ligand

Apo-2 ligand, as disclosed in the present specification, can be employed therapeutically to induce apoptosis in mammalian cells. Generally, the methods for inducing apoptosis in mammalian cells comprise exposing the cells to an effective amount of Apo-2 ligand. This can be accomplished in vivo or ex vivo in accordance, for instance, with the methods described below and in the Examples. It is contemplated that the methods for inducing apoptosis can be employed in therapies for particular pathological conditions which are characterized by decreased levels of apoptosis. Examples of such pathological conditions include autoimmune disorders like lupus and immune-mediated glomerular nephritis, and cancer. Therapeutic application of Apo-2 ligand for the treatment of cancer is described in detail below.

In the methods for treating cancer, Apo-2 ligand is administered to a mammal diagnosed as having cancer. It is of course contemplated that the Apo-2 ligand can be employed in combination with still other therapeutic compositions and techniques, including other apoptosis-inducing agents, chemotherapy, radiation therapy, and surgery.

The Apo-2 ligand is preferably administered to the mammal in a pharmaceutically-acceptable carrier. Suitable carriers and their formulations are described in *Remington's Pharmaceutical Sciences,* 16th ed., 1980, Mack Publishing Co., edited by Oslo et al. Typically, an appropriate amount of a pharmaceutically-acceptable salt is used in the formulation to render the formulation isotonic. Examples of the pharmaceutically-acceptable carrier include saline, Ringer's solution and dextrose solution. The pH of the solution is preferably from about 5 to about 8, and more preferably from about 7.4 to about 7.8. It will be apparent to those persons skilled in the art that certain carriers may be more preferable depending upon, for instance, the route of administration and concentration of Apo-2 ligand being administered.

The Apo-2 ligand can be administered to the mammal by injection (e.g., intravenous, intraperitoneal, subcutaneous, intramuscular), or by other methods such as infusion that ensure its delivery to the bloodstream in an effective form. It is also contemplated that the Apo-2 ligand can be administered by in vivo or ex vivo gene therapy.

Effective dosages and schedules for administering Apo-2 ligand may be determined empirically, and making such determinations is within the skill in the art. It is presently believed that an effective dosage or amount of Apo-2 ligand used alone may range from about 1 µg/kg to about 100 mg/kg of body weight or more per day. Interspecies scaling of dosages can be performed in a manner known in the art, e.g., as disclosed in Mordenti et al., *Pharmaceut. Res.*, 8:1351 (1991). Those skilled in the art will understand that the dosage of Apo-2 ligand that must be administered will vary depending on, for example, the mammal which will receive the Apo-2 ligand, the route of administration, and other drugs or therapies being administered to the mammal.

The one or more other therapies administered to the mammal may include but are not limited to, chemotherapy and radiation therapy, immunoadjuvants, cytokines, and antibody-based therapies. Examples interleukins (e.g., IL-1, IL-2, IL-3, IL-6), leukemia inhibitory factor, interferons, TGF-beta, erythropoietin, thrombopoietin, and HER-2 antibody. Other agents known to induce apoptosis in mammalian cells may also employed, and such agents include TNF-α, TNF-β (lymphotoxin-α), CD30 ligand, 4-1BB ligand, and Apo-1 ligand.

Chemotherapies contemplated by the invention include chemical substances or drugs which are known in the art and are commercially available, such as Doxorubicin, 5-Fluorouracil, Cytosine arabinoside ("Ara-C"), Cyclophosphamide, Thiotepa, Busulfan, Cytoxin, Taxol, Methotrexate, Cisplatin, Melphalan, Vinblastine and Carboplatin. Preparation and dosing schedules for such chemotherapy may be used according to manufacturers' instructions or as determined empirically by the skilled practitioner. Preparation and dosing schedules for such chemotherapy are also described in Chemotherapy Service Ed., M. C. Perry, Williams & Wilkins, Baltimore, Md. (1992).

The chemotherapy is preferably administered in a pharmaceutically-acceptable carrier, such as those described above for Apo-2 ligand. The mode of administration of the chemotherapy may be the same as employed for the Apo-2 ligand or it may be administered to the mammal via a different mode. For example, the Apo-2 ligand may be injected while the chemotherapy is administered orally to the mammal.

Radiation therapy can be administered to the mammal according to protocols commonly employed in the art and known to the skilled artisan. Such therapy may include cesium, iridium, iodine, or cobalt radiation. The radiation therapy may be whole body irradiation, or may be directed locally to a specific site or tissue in or on the body. Typically, radiation therapy is administered in pulses over a period of time from about 1 to about 2 weeks. The radiation therapy may, however, be administered over longer periods of time. Optionally, the radiation therapy may be administered as a single dose or as multiple, sequential doses.

The Apo-2 ligand and one or more other therapies may be administered to the mammal concurrently or sequentially.

Following administration of Apo-2 ligand and one or more other therapies to the mammal, the mammal's cancer and physiological condition can be monitored in various ways well known to the skilled practitioner. For instance, tumor mass may be observed physically, by biopsy or by standard x-ray imaging techniques.

It is contemplated that Apo-2 ligand can be employed to treat cancer cells ex vivo. Such ex vivo treatment may be useful in bone marrow transplantation and particularly, autologous bone marrow transplantation. For instance, treatment of cells or tissue(s) containing cancer cells with Apo-2 ligand, and optionally, with one or more other therapies, such as described above, can be employed to induce apoptosis and substantially deplete the cancer cells prior to transplantation in a recipient mammal.

Cells or tissue(s) containing cancer cells are first obtained from a donor mammal. The cells or tissue(s) may be obtained surgically and preferably, are obtained aseptically. In the method of treating bone marrow for transplantation, bone marrow is obtained from the mammal by needle aspiration. The cells or tissue(s) containing cancer cells are then treated with Apo-2 ligand, and optionally, with one or more other therapies, such as described above. Bone marrow is preferably fractionated to obtain a mononuclear cell fraction (such as by centrifugation over ficoll-hypaque gradient) prior to treatment with Apo-2 ligand.

The treated cells or tissue(s) can then be infused or transplanted into a recipient mammal. The recipient mammal may be the same individual as the donor mammal or may be another, heterologous mammal. For an autologous bone marrow transplant, the mammal is treated prior to the transplant with an effective dose of radiation or chemotherapy as known in the art and described for example in *Autologous Bone Marrow Transplantation: Proceedings of the Third International Symposium*, Dicke et al., eds., University of Texas M.D. Anderson Hospital and Tumor Institute (1987).

C. Non-Therapeutic Uses for Apo-2 Ligand

The Apo-2 ligand of the invention also has utility in non-therapeutic applications. Nucleic acid sequences encoding the Apo-2 ligand may be used as a diagnostic for tissue-specific typing. For example, procedures like in situ hybridization, Northern and Southern blotting, and PCR analysis may be used to determine whether DNA and/or RNA encoding Apo-2 ligand is present in the cell type(s) being evaluated. Apo-2 ligand nucleic acid will also be useful for the preparation of Apo-2 polypeptide by the recombinant techniques described herein.

The isolated Apo-2 ligand may be used in quantitative diagnostic assays as a control against which samples containing unknown quantities of Apo-2 ligand may be prepared. Apo-2 ligand preparations are also useful in generating antibodies, as standards in assays for Apo-2 ligand (e.g., by labeling Apo-2 ligand for use as a standard in a radioimmunoassay, radioreceptor assay, or enzyme-linked immunoassay), in affinity purification techniques for example, in identifying or in isolating a receptor that binds Apo-2 ligand, and in competitive-type receptor binding assays when labeled with, for instance, radioiodine, enzymes, or fluorophores.

D. Anti-Apo-2 Ligand Antibody Preparation

The present invention further provides anti-Apo-2 antibodies. Antibodies against Apo-2 ligand may be prepared as follows. Exemplary antibodies include polyclonal, monoclonal, humanized, bispecific, and heteroconjugate antibodies.

1. Polyclonal Antibodies

The Apo-2 ligand antibodies may comprise polyclonal antibodies. Methods of preparing polyclonal antibodies are known to the skilled artisan. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. The immunizing agent may include the Apo-2 ligand polypeptide or a fusion protein thereof. It may be useful to conjugate the immunizing agent to a protein known to be immunogenic in the mammal being immunized. Examples of such immunogenic proteins which may be employed include but are not limited to keyhole limpet hemocyanin, serum albumin, bovine thyroglobulin, and soybean trypsin inhibitor. An aggregating agent such as alum may also be employed to enhance the mammal's immune response. Examples of adjuvants which may be employed include Freund's complete adjuvant and MPL-TDM adjuvant (monophosphoryl Lipid A, synthetic trehalose dicorynomycolate). The immunization protocol may be selected by one skilled in the art without undue experimentation. The mammal can then be bled, and the serum assayed for antibody titer. If desired, the mammal can be boosted until the antibody titer increases or plateaus.

2. Monoclonal Antibodies

The Apo-2 ligand antibodies may, alternatively, be monoclonal antibodies. Monoclonal antibodies may be prepared using hybridoma methods, such as those described by Kohler and Milstein, *Nature*, 256:495 (1975). In a hybridoma method, a mouse, hamster, or other appropriate host animal, is typically immunized (such as described above) with an immunizing agent to elicit lymphocytes that produce or are capable of producing antibodies that will specifically bind to the immunizing agent. Alternatively, the lymphocytes may be immunized in vitro.

The immunizing agent will typically include the Apo-2 ligand polypeptide or a fusion protein thereof. Cells expressing Apo-2 ligand at their surface may also be employed. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell [Goding, *Monoclonal Antibodies: Principles and Practice*, Academic Press, (1986) pp. 59–103]. Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of human monoclonal antibodies [Kozbor, *J. Immunol.*, 133:3001 (1984); Brodeur et al., *Monoclonal Antibody Production Techniques and Applications*, Marcel Dekker, Inc., New York, (1987) pp. 51–63].

The culture medium in which the hybridoma cells are cultured can then be assayed for the presence of monoclonal antibodies directed against Apo-2 ligand. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art, and are described further in the Examples below. The binding affinity of the monoclonal antibody can, for example, be determined by the Scatchard analysis of Munson and Pollard, *Anal. Biochem.*, 107:220 (1980).

After the desired hybridoma cells are identified, the clones may be subcloned by limiting dilution procedures and grown by standard methods [Goding, supra]. Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences [U.S. Pat. No. 4,816,567; Morrison et al., supra] or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

The antibodies may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof, particularly, Fab fragments, can be accomplished using routine techniques known in the art. For instance, digestion can be performed using papain. Examples of papain digestion are described in WO 94/29348 published Dec. 22, 1994 and U.S. Pat. No. 4,342,566. Papain digestion of antibodies typically produces two identical antigen binding fragments, called Fab fragments, each with a single antigen binding site, and a residual Fc fragment. Pepsin treatment yields an F(ab')$_2$ fragment that has two antigen combining sites and is still capable of cross-linking antigen.

The Fab fragments produced in the antibody digestion also contain the constant domains of the light chain and the first constant domain (CH$_1$) of the heavy chain. Fab' fragments differ from Fab fragments by, the addition of a few residues at the carboxy terminus of the heavy chain CH$_1$ domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

3. Humanized Antibodies

The Apo-2 ligand antibodies of the invention may further comprise humanized antibodies or human antibodies. Humanized forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., *Nature,* 321:522–525 (1986); Reichmann et al., *Nature,* 332:323–329 (1988); and Presta, *Curr. Op. Struct. Biol.,* 2:593–596 (1992)].

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers [Jones et al., *Nature,* 321:522–525 (1986); Riechmann et al., *Nature,* 332:323–327 (1988); Verhoeyen et al., *Science,* 239:1534–1536 (1988)], by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important in order to reduce antigenicity. According to the "best-fit" method, the sequence of the variable domain of a rodent antibody is screened against the entire library of known human variable domain sequences. The human sequence which is closest to that of the rodent is then accepted as the human framework (FR) for the humanized antibody [Sims et al., *J. Immunol.,* 151:2296 (1993); Chothia and Lesk, *J. Mol. Biol.,* 196:901 (1987)]. Another method uses a particular framework derived from the consensus sequence of all human antibodies of a particular subgroup of light or heavy chains. The same framework may be used for several different humanized antibodies [Carter et al., *Proc. Natl. Acad. Sci. USA,* 89:4285 (1992); Presta et al., *J. Immunol.,* 151:2623 (1993)].

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three dimensional models of the parental and humanized sequences. Three dimensional immunoglobulin models are commonly available and are familiar to those skilled in the art.

Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequence so that the desired antibody characteristic, such as increased affinity for the target antigen(s), is achieved. In general, the CDR residues are directly and most substantially involved in influencing antigen binding [see, WO 94/04679 published 3 Mar. 1994].

Transgenic animals (e.g., mice) that are capable, upon immunization, of producing a full repertoire of human antibodies in the absence of endogenous immunoglobulin production can be employed. For example, it has been described that the homozygous deletion of the antibody heavy chain joining region (J$_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge [see, e.g., Jakobovits et al., *Proc. Natl. Acad. Sci. USA,* 90:2551–255 (1993); Jakobovits et al., *Nature,* 362:255–258 (1993); Bruggermann et al., *Year in Immuno.,* 7:33 (1993)]. Human antibodies can also be produced in phage display libraries [Hoogenboom and Winter, *J. Mol. Biol.,* 227:381 (1991); Marks et al., *J. Mol. Biol.,* 222:581 (1991)]. The techniques of Cote et al. and Boerner et al. are also available for the preparation of human monoclonal antibodies (Cote et al., *Monoclonal Antibodies and Cancer Therapy,* Alan R. Liss, p. 77 (1985) and Boerner et al., *J. Immunol.,* 147(1):86–95 (1991).

4. Bispecific Antibodies

Bispecific antibodies are monoclonal, preferably human or humanized, antibodies that have binding specificities for at least two different antigens. In the present case, one of the binding specificities is for the Apo-2 ligand, the other one is for any other antigen, and preferably for a cell-surface protein or receptor or receptor subunit.

Methods for making bispecific antibodies are known in the art. Traditionally, the recombinant production of bispecific antibodies is based on the co-expression of two immunoglobulin heavy-chain/light-chain pairs, where the two heavy chains have different specificities [Millstein and Cuello, *Nature*, 305:537–539 (1983)]. Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published 13 May 1993, and in Traunecker et al., *EMBO J.*, 10:3655–3659 (1991).

According to a different and more preferred approach, antibody variable domains with the desired binding specificities (antibody-antigen combining sites) are fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance. In a preferred embodiment of this approach, the bispecific antibodies are composed of a hybrid immunoglobulin heavy chain with a first binding specificity in one arm, and a hybrid immunoglobulin heavy-chain/light-chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690 published 3 Mar. 1994. For further details of generating bispecific antibodies see, for example, Suresh et al., *Methods in Enzymology*, 121:210 (1986).

5. Heteroconjugate Antibodies

Heteroconjugate antibodies are also within the scope of the present invention. Heteroconjugate antibodies are composed of two covalently joined antibodies. Such antibodies have, for example, been proposed to target immune system cells to unwanted cells [U.S. Pat. No. 4,676,980], and for treatment of HIV infection [WO 91/00360; WO 92/200373; EP 03089]. It is contemplated that the antibodies may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

E. Uses of Apo-2 Ligand Antibodies

Apo-2 ligand antibodies may be used in diagnostic assays for Apo-2 ligand, e.g., detecting its expression in specific cells, tissues, or serum. Various diagnostic assay techniques known in the art may be used, such as competitive binding assays, direct or indirect sandwich assays and immunoprecipitation assays conducted in either heterogeneous or homogeneous phases [Zola, *Monoclonal Antibodies: A Manual of Techniques*, CRC Press, Inc. (1987) pp. 147–158]. The antibodies used in the diagnostic assays can be labeled with a detectable moiety. The detectable moiety should be capable of producing, either directly or indirectly, a detectable signal. For example, the detectable moiety may be a radioisotope, such as $^3$H, $^{14}$C, $^{32}$P, $^{35}$S, or 125I, a fluorescent or chemiluminescent compound, such as fluorescein isothiocyanate, rhodamine, or luciferin, or an LS enzyme, such as alkaline phosphatase, beta-galactosidase or horseradish peroxidase. Any method known in the art for conjugating the antibody to the detectable moiety may be employed, including those methods described by Hunter et al., *Nature*, 144:945 (1962); David et al., *Biochemistry*, 13:1014 (1974); Pain et al., *J. Immunol. Meth.*, 40:219 (1981); and Nygren, *J. Histochem. and Cytochem.*, 30:407 (1982).

Apo-2 ligand antibodies also are useful for the affinity purification of Apo-2 ligand from recombinant cell culture or natural sources. In this process, the antibodies against Apo-2 ligand are immobilized on a suitable support, such a Sephadex resin or filter paper, using methods well known in the art. The immobilized antibody then is contacted with a sample containing the Apo-2 ligand to be purified, and thereafter the support is washed with a suitable solvent that will remove substantially all the material in the sample except the Apo-2 ligand, which is bound to the immobilized antibody. Finally, the support is washed with another suitable solvent that will release the Apo-2 ligand from the antibody. Apo-2 ligand antibodies also are useful for the affinity purification of a solubilized Apo-2 receptor or for expression cloning of an Apo-2 receptor.

F. Kits Containing Apo-2 Ligand or Apo-2 Ligand Antibodies

In a further embodiment of the invention, there are provided articles of manufacture and kits containing Apo-2 ligand or Apo-2 ligand antibodies which can be used, for instance, for the therapeutic or non-therapeutic applications described above. The article of manufacture comprises a container with a label. Suitable containers include, for example, bottles, vials, and test tubes. The containers may be formed from a variety of materials such as glass or plastic. The container holds a composition which includes an active agent that is effective for therapeutic or non-therapeutic applications, such as described above. The active agent in the composition is Apo-2 ligand or an Apo-2 ligand antibody. The label on the container indicates that the composition is used for a specific therapy or non-therapeutic application, and may also indicate directions for either in vivo or in vitro use, such as those described above.

The kit of the invention will typically comprise the container described above and one or more other containers comprising materials desirable from a commercial and user standpoint, including buffers, diluents, filters, needles, syringes, and package inserts with instructions for use.

The following examples are offered for illustrative purposes only, and are not intended to limit the scope of the present invention in any way.

All references cited in the present specification are hereby incorporated by reference in their entirety.

EXAMPLES

All restriction enzymes referred to in the examples were purchased from New England Biolabs and used according to manufacturer's instructions. All other commercially available reagents referred to in the examples were used according to manufacturer's instructions unless otherwise indicated. The source of those cells identified in the following examples, and throughout the specification, by ATCC accession numbers is the American Type Culture Collection, Manassas, Va.

Example 1

Isolation of cDNA Clones Encoding Human Apo-2 Ligand

To isolate a full-length cDNA for Apo-2 ligand, a lambda gt11 bacteriophage library of human placental cDNA (about 1×10⁶ clones) (HL10756, commercially available from Clontech) was screened by hybridization with synthetic oligonucleotide probes based on an EST sequence (GenBank locus HHEA47M), which showed some degree of homology to human Fas/Apo-1 ligand. The EST sequence of HHEA47M is 390 bp and when translated in its +3 frame, shows 16 identities to a 34 amino acid region of human Apo-1 ligand. The sequence of HHEA47M is as follows:

```
GGGACCCCAATGACGAAGAGAGTATGAACAGCCCCTGCTGGCAAGTCAAGTGGCAACTCCGTCAG  SEQ ID NO:3

CTCGTTAGAAAGATGATTTTGAGAACCTCTGAGGAAACCATTTCTACAGTTCAAGAAAAGCAACA

AAATATTTCTCCCCTAGTGAGAGAAAGAGGTCCTCAGAGAGTAGCAGCTCACATAACTGGGACCA

GAGGAAGAAGCAACACATTGTCTTCTCCAAACTCCAAGAATGAAAAGGCTCTGGGCCGCAAAATA

AACTCCTGGGAATCATCAAGGAGTGGGCATTCATTCCTGAGCAACTTGCACTTGAGGAATGGTGA

ACTGGTCATCCATGAAAAAGGGTTTTACTACATCTATTCCCAAACATACTTTCGATTTCAGGAGG
```

A 60 bp oligonucleotide probe with the following sequence was employed in the screening:

```
TGACGAAGAGAGTATGAACAGCCCCTGCTGGCAAGTCAAGTGGCAACTCCGTCAGCTCGT  SEQ ID NO:4
```

Hybridization was conducted overnight at room temperature in buffer containing 20% formamide, 5×SSC, 10% dextran sulfate, 0.1% NaPiPO₄, 0.05M NaPO₄, 0.05 mg salmon sperm DNA, and 0.1% sodium dodecyl sulfate, followed by several washes at 42° C. in 5× SSC, and then in 2× SSC. Twelve positive clones were identified in the cDNA library, and the positive clones were rescreened by hybridization to a second 60 bp oligonucleotide probe (not overlapping the first probe) having the following sequence:

```
GGTGAACTGGTCATCCATGAAAAAGGGTTTTACTACATCTATTCCCAAACATACTTTCGA  SEQ ID NO:5
```

Hybridization was conducted as described above.

Four resulting positive clones were identified and amplified by polymerase chain reaction (PCR) using a primer based on the flanking 5' vector sequence and adding an external ClaI restriction site and a primer based on the 3' flanking vector sequence and adding an external HindIII restriction site. PCR products were gel purified and subcloned into pGEM-T (commercially available from Promega) by T-A ligation. Three independent clones from different PCRs were then subjected to dideoxy DNA sequencing. DNA sequence analysis of these clones demonstrated that they were essentially identical, with some length variation at their 5' region.

The nucleotide sequence of the coding region of Apo-2 ligand is shown in FIG. 1A. Sequencing of the downstream 3' end region of one of the clones revealed a characteristic polyadenylation site (data not shown). The cDNA contained one long open reading frame with an initiation site assigned to the ATG codon at nucleotide positions 91–93. The surrounding sequence at this site is in reasonable agreement with the proposed consensus sequence for initiation sites [Kozak, *J. Cell. Biol.*, 115:887–903 (1991)]. The open reading frame ends at the termination codon TAA at nucleotide positions 934–936.

The predicted mature amino acid sequence of human Apo-2 ligand contains 281 amino acids, and has a calculated molecular weight of approximately 32.5 kDa and an isoelectric point of approximately 7.63. There is no apparent signal sequence at the N-terminus, although hydropathy analysis (data not shown) indicated the presence of a hydrophobic region between residues 15 and 40. The absence of a signal sequence and the presence of an internal hydrophobic region suggests that Apo-2 ligand is a type II transmembrane protein. The putative cytoplasmic, transmembrane and extracellular regions are 14, 26 and 241 amino acids long, respectively. The putative transmembrane region is underlined in FIG. 1A. A potential N-linked glycosylation site is located at residue 109 in the putative extracellular domain.

An alignment (using the Align™ computer program) of the amino acid sequence of the C-terminal region of Apo-2 ligand with other known members of the TNF cytokine family showed that, within the C-terminal region, Apo-2 ligand exhibits 23.2% identity to Apo-1 ligand (FIG. 1B). The alignment analysis showed a lesser degree of identity with other TNF family members: CD40L (20.8%), LT-α (20.2%), LT-α (19.6%), TNF-α (19.0%), CD30L and CD27L (15.5%) OX-40L (14.3%), and 4-1BBL (13.7%). In the TNF cytokine family, residues within regions which are predicted to form β strands, based on the crystal structures of TNF-α and LT-β [Eck et al., *J. Bio. Chem.,* 264:17595–17605 (1989); Eck et al., *J. Bio. Chem.,* 267: 2119–2122 (1992)], tend to be more highly conserved with other TNF family members than are residues in the predicted connecting loops. It was found that Apo-2 ligand exhibits greater homology to other TNF family members in its putative β strand regions, as compared to homology in the predicted connecting loops. Also, the loop connecting putative β strands, B and B', is markedly longer in Apo-2 ligand.

Example 2

Expression of Human APO-2 Ligand

A. Full-length cDNA Fusion Construct

A full-length Apo-2 ligand cDNA fused to a myc epitope tag was constructed as follows. The Apo-2 ligand cDNA insert was excised from the parental pGEM-T Apo-2 ligand plasmid (described in Example 1) by digestion with ClaI and HindIII, and inserted into a pRK5 mammalian expression plasmid [Schall et al., *Cell,* 61:361–370 (1990); Suva et al., *Science,* 237:893–896 (1987)], which was digested with the same restriction enzymes. A sequence encoding a 13 amino acid myc epitope tag Ser Met Glu Gln Lys Leu Ile Ser Glu Glu Asp Leu Asn SEQ ID NO:6.

[Evan et al., *Mol. Cell. Biol.,* 5:3610–3616 (1985)] was then inserted between codon 281 and the stop codon (codon 282) at the 3' end of the Apo-2 ligand coding sequence by oligonucleotide directed mutagenesis [Zoller et al., *Nucleic Acids Res.,* 10:6487–6496 (1982)] to give plasmid pRK5 Apo-2 ligand-myc.

The pRK5 Apo-2 ligand-myc plasmid was co-transfected into human 293 cells (ATCC CRL 1573) with a pRK5 plasmid carrying a neomycin resistance gene, by calcium phosphate precipitation. Stable clones expressing Apo-2 ligand-myc were selected by ability to grow in 50' HAM's F12/50' DMEM (GIBCO) media in the presence of the antibiotic, G418 (0.5 mg/mL) (GIBCO).

To investigate the topology of Apo-2 ligand, a G418-resistant clone was analyzed by FACS after staining with anti-myc monoclonal antibody, (mAb) clone 9E10 [Evan et al., supra; commercially available from Oncogene Science) followed by a phycoerythrin (PE)-conjugated goat anti-mouse antibody (commercially available from Jackson ImmunoResearch). The FACS analysis revealed a specific positive staining shift in the Apo-2 ligand-myc-transfected clone as compared to mock transfected cells (FIG. 1C), showing that Apo-2 ligand is expressed at the cell-surface, with its carboxy terminus exposed. Accordingly, Apo-2 ligand is believed to be a type II transmembrane protein.

B. ECD Fusion Constructs

Two soluble Apo-2 ligand extracellular domain ("ECD") fusion constructs were prepared, in which another sequence was fused upstream of the C-terminal region of Apo-2 ligand.

In one construct, 27 amino acids of the herpes virus glycoprotein D ("gD") signal peptide [described in Lasky et al., *DNA,* 3:23–29 (1984); Pennica et al., *Proc. Natl. Acad. Sci.,* 92:1142–1146 (1995); Paborsky et al., *Protein Engineerinq,* 3:547–553 (1990)] and epitope tag sequence Lys Tyr Ala Leu Ala Asp Ala Ser Leu Lys Met Ala Asp Pro
Asn Arg Phe Arg Gly Lys Asp Leu Pro Val Leu Asp Gln
SEQ ID NO:7 were fused upstream to codons 114–281 of Apo-2 ligand within a pRK5 mammalian expression plasmid. Briefly, the gD sequence was amplified from a parent plasmid, pCHAD (Genentech, prepared substantially as described in Lasky et al., *Science,* 233:209–212 (1986)), in a PCR in which the 3' primer was complementary to the 3' region of the gD sequence as well as to codons 114–121 of Apo-2 ligand. The product was used as a 5, primer along with a 3' primer complementary to the 3' end of the Apo-2 ligand-coding region in a subsequent PCR in which the pRK5 Apo-2 ligand plasmid was used as a template. The product, encoding the gD-Apo-2 ligand ECD fusion was then subcloned into a pRK5 plasmid to give the plasmid pRK5 gD-Apo-2 ligand ECD.

Human embryonic kidney 293 cells (ATCC CRL 1573) were transiently transfected with the pRK5 gD-Apo-2 ligand ECD plasmid or with pRK5, by calcium phosphate precipitation. Expression of soluble gD-Apo-2 ligand protein was assessed by metabolic labeling of the transfected cells with 35-Cys and $^{35}$S-Met. Cell supernatants were collected after 24 hours and cleared by centrifugation. For immunoprecipitation, 5 ml of supernatant were incubated with 5B6 anti-gD monoclonal antibody (Genentech) at 1 μg/ml overnight at 4° C. Then, 25 μl Pansorbin (Sigma) was added for another 1 hour at 4° C. The tubes were spun, the pellets were washed in PBS and boiled for 5 minutes in SDS sample buffer. The boiled samples were spun again, and the supernatants were subjected to SDS-PAGE and autoradiography.

Immunoprecipitation with anti-gD antibody revealed three predominant protein bands in the supernatants of cells transfected with the gD-Apo-2 ligand plasmid (FIG. 1E). These bands migrated with relative molecular masses (Mr) of 23, 48 and 74 kDa. The calculated molecular weight of the mature gD-Apo-2 polypeptide is approximately 22.5 kDa; hence, the observed bands may represent monomeric (23 kDa), dimeric (48 kDa) and trimeric (74 kDa) forms of the fusion protein, and indicate that Apo-2 ligand can be expressed as a secreted soluble gD fusion protein in mammalian cells.

In a second construct, a Met Gly $His_{10}$ sequence (derived from the plasmid pET19B, Novagen), followed by a 12 amino acid enterokinase cleavage site Met Gly His His His His His His His His His His Ser Ser Gly
His Ile Asp Asp Asp Asp Lys His Met
SEQ ID NO:8 was fused upstream to codons 114–281 of Apo-2 ligand within a baculovirus expression plasmid (pVL1392, Pharmingen). Briefly, the Apo-2 ligand codon 114–281 region was amplified by PCR from the parent pRK5 Apo-2 ligand plasmid (described in Example 1) with primers complementary to the 5' and 3' regions which incorporate flanking NdeI and BamHI restriction sites respectively. The product was subcloned into pGEM-T (Promega) by T-A ligation, and the DNA sequence was confirmed. The insert was then excised by digestion with NdeI and BamHI and subcloned into a modified baculovirus expression vector pVL1392 (commercially available from Pharmingen) containing an amino terminal Met Gly $His_{10}$ tag and enterokinase cleavage site.

Recombinant baculovirus was generated by co-transfecting the $His_{10}$-Apo-2 ECD plasmid and BaculoGold™ virus DNA (Pharmingen) into *Spodoptera frugiperda* ("Sf9") cells (ATCC CRL 1711) using lipofectin (commercially available from GIBCO-BRL). After 4–5 days of incubation at 28° C., the released viruses were harvested and used for further amplifications. Viral infection and protein expression was performed as described by O'Reilley et al., Baculovirus expression vectors: A laboratory Manual, Oxford:Oxford University Press (1994). The protein was purified by $Ni^{2+}$-chelate affinity chromatography, as described in Example 3 below.

Example 3

Purification of Recombinant Human Apo-2 Ligand

Extracts were prepared from recombinant virus-infected and mock-infected Sf9 cells (see Example 2, section B above) as described by Rupert et al., *Nature*, 362:175–179 (1993). Briefly, Sf9 cells were washed, resuspended in sonication buffer (25 mL Hepes, pH 7.9; 12.5 mM $MgCl_2$; 0.1 mM EDTA; 10% Glycerol; 0.1 NP-40; 0.4 M KCl), and sonicated twice for 20 seconds on ice. The sonicates were cleared by centrifugation, and the supernatant was diluted 50-fold in loading buffer (50 mM phosphate, 300 mM NaCl, 10% Glycerol, pH 7.8) and filtered through a 0.45 μm filter. A $Ni^{2+}$-NTA agarose column (commercially available from Qiagen) was prepared with a bed volume of 5 mL, washed with 25 mL of water and equilibrated with 25 mL of loading buffer. The filtered cell extract was loaded onto the column at 0.5 mL per minute. The column was washed to baseline $A_{280}$ with loading buffer, at which point fraction collection was started. Next, the column was washed with a secondary wash buffer (50 mM phosphate; 300 mM NaCl, 10% Glycerol, pH 6.0), which eluted nonspecifically bound protein. After reaching $A_{280}$ baseline again, the column was developed with a 0 to 500 mM Imidazole gradient in the secondary wash buffer. One mL fractions were collected and analyzed by SDS-PAGE and silver staining or western blot with $Ni^{2+}$-NTA-conjugated to alkaline phosphatase (Qiagen). Fractions containing the eluted $His_{10}$-Apo-2 ligand protein were pooled and dialyzed against loading buffer.

An identical procedure was repeated with mock-infected Sf9 cells as the starting material, and the same fractions were pooled, dialyzed, and used as control for the purified human Apo-2.

SDS-PAGE analysis of the purified protein revealed a predominant band of Mr 24 kDa, corresponding with the calculated molecular weight of 22.4 kDa for the $His_{10}$-Apo-2 ligand monomer (FIG. 1D, lane 3); protein sequence microanalysis (data not shown) confirmed that the 24 kDa band represents the $His_{10}$-Apo-2 ligand polypeptide. Minor 48 kDa and 66 kDa bands were also observed, and probably represent soluble Apo-2 ligand homodimers and homotrimers. Chemical crosslinking of the purified $His_{10}$-Apo-2 ligand by incubation with sulfo-NHS (5 mM) (Pierce Chemical) and EDC (Pierce Chemical) at 25 mM and 50 mM (FIG. 1D, lanes 1 and 2, respectively), shifted the protein into the 66 kDa band primarily. These results suggest that the predominant form of Apo-2 ligand in solution is homotrimeric and that these trimers dissociate into dimers and monomers in the presence of SDS.

Example 4

Apoptotic Activity of Apo-2 Ligand on Human Lymphoid Cell Lines

Apoptotic activity of purified, soluble Apo-2 ligand (described in Example 3) was examined using several human lymphoid cell lines. In a first study, the effect of Apo-2 ligand on 9D cells (Genentech, Inc.), derived from Epstein-Barr virus (EBV)-transformed human peripheral blood B cells, was examined. The 9D cells ($5 \times 10^4$ cells/well in RPMI 1640 medium plus 10% fetal calf serum) were incubated for 24 hours with either a media control, Apo-2 ligand (3 μg/ml, prepared as described in Example 3 above), or anti-Apo-1 monoclonal antibody, CH11 (1 μg/ml) [described by Yonehara et al., *J. Exp. Med.*, 169:1747–1756 (1989); commercially available from Medical and Biological Laboratories Co.]. The CH11 anti-Apo-1 antibody is an agonistic antibody which mimicks Fas/Apo-1 ligand activity.

After the incubation, the cells were collected onto cytospin glass slides, and photographed under an inverted light microscope. Both Apo-2 ligand and the anti-Apo-1 monoclonal antibody induced a similar apoptotic effect, characterized by cytoplasmic condensation and reduction in cell numbers. (see FIG. 2A).

The effects of the Apo-2 ligand on the 9D cells, as well as on Raji cells (human Burkitt's lymphoma B cell line, ATCC CCL 86) and Jurkat cells (human acute T cell leukemia cell line, ATCC TIB 152) were further analyzed by FACS. The FACS analysis was conducted, using established criteria for apoptotic cell death, namely, the relation of fluorescence staining of the cells with two markers: (a) propidium iodide ("PI") dye, which stains apoptotic but not live cells, and (b) a fluorescent derivative of the protein, annexin V, which binds to the exposed phosphatidylserine found on the surface of apoptotic cells, but not on live cells [Darzynkiewicz et al., *Methods in Cell Biol.*, 41:15–38 (1994); Fadok et al., *J. Immunol.*, 148:2207–2214 (1992); Koopman et al., *Blood*, 84:1415–1420 (1994)].

The 9D cells (FIG. 2B), Raji cells (FIG. 2C), and Jurkat cells (FIG. 2D) were incubated ($1 \times 10^6$ cells/well) for 24 hours with a media control (left panels), Apo-2 ligand (3 μg/ml, prepared as described in Example 3) (center panels), or anti-Apo-1 ligand antibody, CH11 (1 μg/ml) (right panels). The cells were then washed, stained with PI and with fluorescein thiocyanate (FITC)-conjugated annexin V (purchased from Brand Applications) and analyzed by flow cytometry. Cells negative for both PI and annexin V staining (quadrant 3) represent live cells; PI-negative, annexin V-positive staining cells (quadrant 4) represent early apoptotic cells; PI-positive, annexin V-positive staining cells (quadrant 2) represent primarily cells in late stages of apoptosis.

Figure 2B:
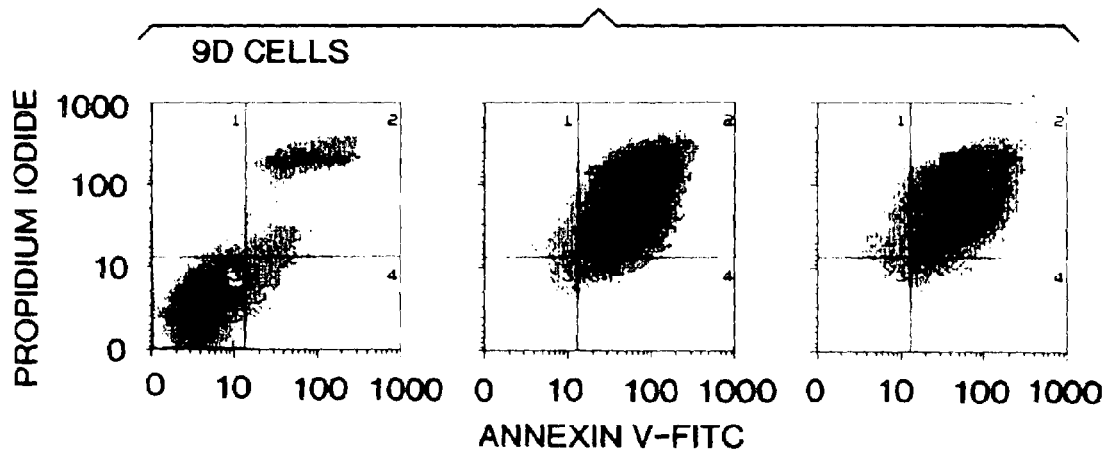
Figure 2C:
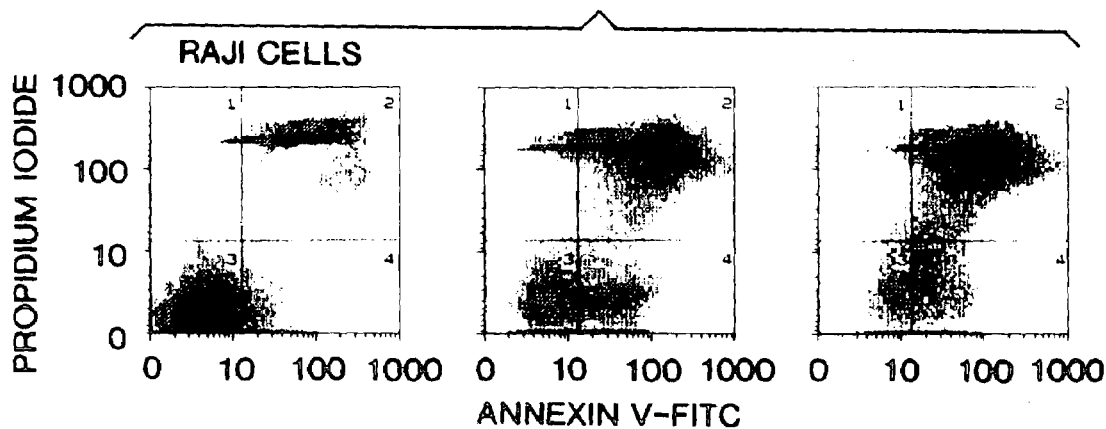
Figure 2D:
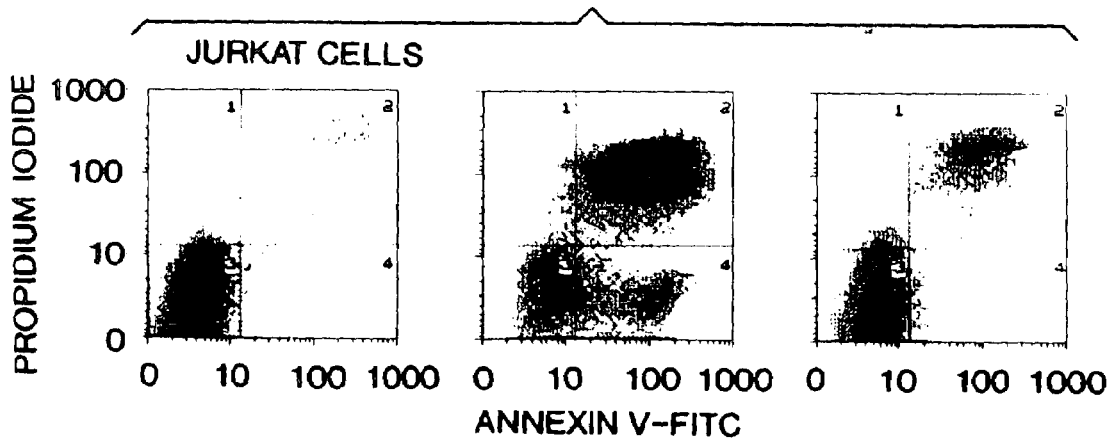

The Apo-2 ligand treated 9D cells exhibited elevated extracellular annexin V binding, as well as a marked increase in uptake of PI (FIG. 2B), indicating that Apo-2 ligand induced apoptosis in the cells. Comparable results were obtained with anti-Apo-1 antibody, CH11 (FIG. 2B). The Apo-2 ligand induced a similar response in the Raji and Jurkat cells, as did the anti-Apo-1 antibody. (see FIGS. 2C and 2D). The induction of apoptosis (measured as the % apoptotic cells) in these cell lines by Apo-2 ligand, as compared to the control and to the anti-Apo-1 antibody, is also shown in Table 1 below.

Figure 2E:
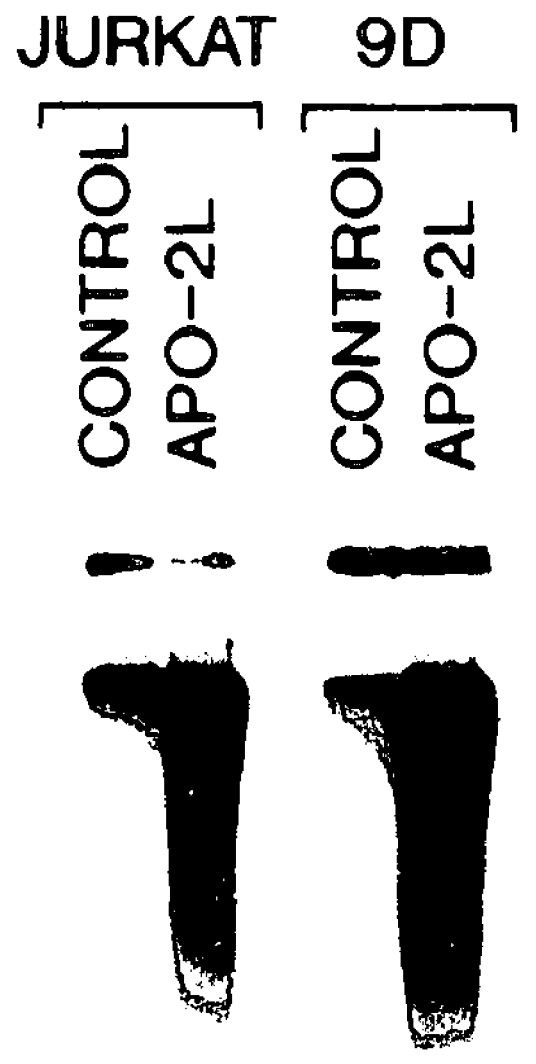

The activation of internucleosomal DNA fragmentation by Apo-2 ligand was also analyzed. Jurkat cells (left lanes) and 9D cells (right lanes) were incubated ($2 \times 10^6$ cells/well) for 6 hours with a media control or Apo-2 ligand (3 μg/ml, prepared as described in Example 3), The DNA was then extracted from the cells and labeled with $^{32}$P-ddATP using terminal transferase. The labeled DNA samples were subjected to electrophoresis on 21 agarose gels and later analyzed by autoradiography [Moore et al., *Cytotechnology*, 17:1–11 (1995)]. The Apo-2 ligand induced internucleosomal DNA fragmentation in both the Jurkat cells and 9D cells (FIG. 2E). Such DNA fragmentation is characteristic of apoptosis [Cohen, *Advances in Immunol.*, 50:55–85 (1991)].

To examine the time-course of the Apo-2 ligand apoptotic activity, 9D cells were incubated in microtiter dishes (5×10$^4$ cells/well) with a media control or Apo-2 ligand (3 µg/ml, prepared as described in Example 3) for a period of time ranging from 0 hours to 50 hours. Following the incubation, the numbers of dead and live cells were determined by microscopic examination using a hemocytometer.

Figure 3A:
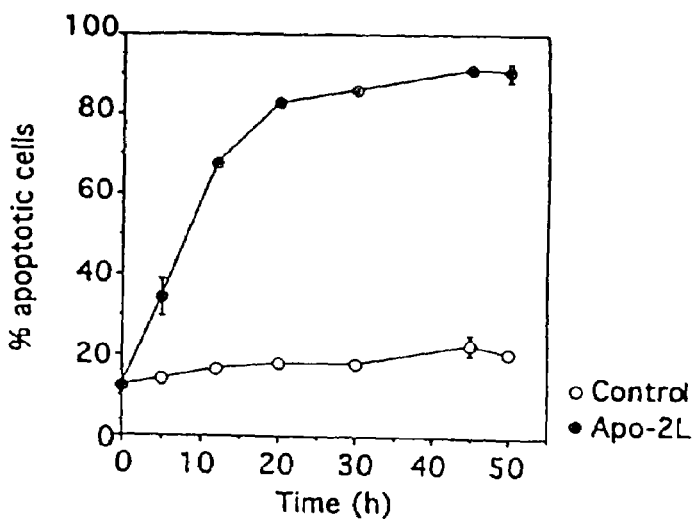
FIGS. 3A–3C show the time course and the dose-dependence of Apo-2 ligand-induced apoptosis and the lack of inhibition of Apo-2 ligand-induced apoptosis by soluble receptor-IgG-fusion proteins based on the Fas/Apo-1 receptor, TNF-R1 receptor, or TNF-R2 receptor.

As shown in FIG. 3A, maximal levels of cell death were induced in 9D cells within 24 hours.

Figure 3B:
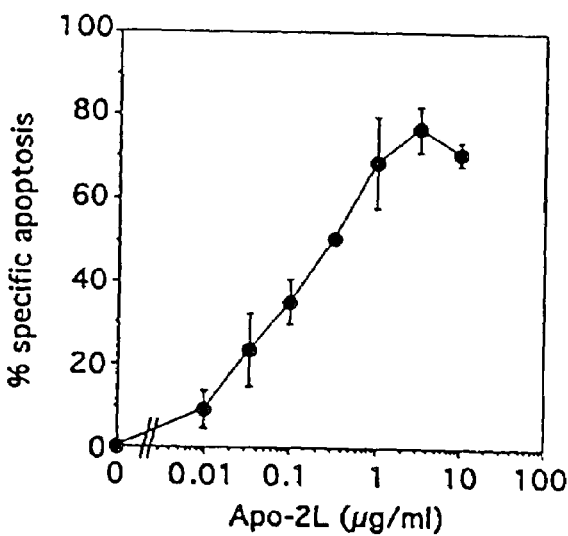

To determine dose-dependency of Apo-2 ligand-induced cell death, 9D cells were incubated (5×10$^4$ cells/well) for 24 hours with serial dilutions of a media control or Apo-2 ligand (prepared as described in Example 3). The numbers of dead and live cells following the incubation were determined as described above. The results are illustrated in FIG. 3B. Specific apoptosis was determined by subtracting the % apoptosis in the control from % apoptosis in Apo-2 ligand treated cells. Half-maximal activation of apoptosis occurred at approximately 0.1 µg/ml (approximately 1 nM), and maximal induction occurred at about 1 to about 3 µg/ml (approximately 10 to 30 nM).

Example 5

Apoptotic Activity of Apo-2 Ligand on Human Non-Lymphoid Tumor Cell Lines

The effect of Apo-2 ligand on human non-lymphoid tumor cell lines was examined using the following cell lines: HeLa (derived from human cervical carcinoma, ATCC CCL 22); ME-180 (derived from human cervical carcinoma, ATCC HTB 33); MCF7 (derived from human breast carcinoma, ATCC HTB 22); U-937 (derived from human hystiocytic lymphoma, ATCC CRL 1593); A549 (derived from human lung carcinoma, ATCC CCL 185); and 293 (derived from an adenovirus-transformed human embryonic kidney cells, ATCC CCL 1573).

In the assay, 1×10$^6$ cells of each cell line were incubated for 24 hours with a media control, Apo-2 ligand (3 µg/ml, prepared as described in Example 3), or anti-Apo-1 monoclonal antibody, CH 11 (1 µg/ml). Following the incubation, apoptosis was measured by FACS analysis, as described in Example 4. The results are shown below in Table 1.

TABLE 1

| Cell line | % apoptotic cells | | |
|---|---|---|---|
| | Control | Apo-2L | Anti-Apo-1 Ab |
| Lymphoid | | | |
| 9D | 22.5 | 92.4 | 90.8 |
| Raji | 35.9 | 73.4 | 82.7 |
| Jurkat | 5.9 | 77.0 | 18.1 |
| Non-lymphoid | | | |
| HeLa | 5.3 | 18.6 | 17.9 |
| MCF7 | 39.9 | 47.3 | 44.0 |
| U-937 | 3.6 | 62.3 | 16.6 |
| A549 | 16.5 | 74.6 | 25.1 |
| ME-180 | 8.6 | 80.7 | 9.9 |
| 293 | 12.3 | 12.2 | 16.7 |

The HeLa cells and MCF7 cells were equally sensitive to induction of apoptosis by Apo-2 ligand as compared to the CH11 anti-Apo-1 antibody. In contrast, the U-937 cells and A549 cells were markedly more sensitive to induction of apoptosis by Apo-2 ligand. The ME-180 cells were quite sensitive to the Apo-2 ligand, but were relatively resistant to the anti-apo-1 antibody. The 293 cells were resistant to the Apo-2 ligand and weakly responsive to the anti-Apo-1 antibody.

Thus, Apo-2 ligand is capable of inducing apoptosis in cells of non-lymphoid origin, as well as cells of lymphoid origin (see Example 4). Also, although not fully understood and not wishing to be bound by any particular theory, Applicants presently believe that Apo-2 ligand acts via a receptor which is distinct from Apo-1. This belief is supported by the data herein showing that the cell lines described above exhibit differential patterns of sensitivity to Apo-2 ligand and to anti-Apo-1 antibody. (see also, Example 7 below).

Example 6

Effect of Apo-2 Ligand on Human Peripheral Blood Monocytes

Peripheral blood mononuclear cells ("PBMC") were isolated from the blood of human donors by Ficoll density gradient centrifugation using. Lymphocyte Separation Medium (LSM®, Organon Teknika). An isolated population of T cells was prepared from the PBMC by removal of B cells through surface Ig binding to an anti-Ig column and removal of monocytes through Fc receptor binding to an Ig column (R & D Systems). An isolated population of B cells was prepared from the PBMC by complement-mediated elimination of T cells reacted with the anti-CD3 antibody produced by the OKT3 myeloma (ATCC, CRL 8001) and of monocytes reacted with a monocyte-specific antibody produced by the 4F2C13 hybridoma (ATCC, HB 22). Additional monocyte removal was accomplished by adherence to plastic.

The freshly isolated peripheral blood B or T cells (1×10$^6$ cells/well) were cultured for 3 days in the presence of a media control or Apo-2 ligand (3 µg/ml, prepared as described in Example 3). For activation, B cells were treated simultaneously with lipopolysaccharide ("LPS", 1 µg/ml), and T cells were treated with phorbol myristate acetate ("PMA", 10 ng/ml) plus ionomycin (1 µg/ml) (Sigma). For interleukin-2 ("IL-2") pretreatment, T cells were cultured for 3–5 days in the presence of IL-2 (50 U/ml) (Genzyme) before exposure to Apo-2 ligand. Apoptosis was determined using FACS analysis essentially as described above in Example 4. However, B cells were gated by anti-CD19/CD20 antibodies (Jackson Immunoresearch), and T cells were gated by anti-CD4/CD8 antibodies (Jackson Immunoresearch). The results are shown in Table 2 below, representing means±SE of independent experiments [B lymphocytes—9 experiments; T lymphocytes—8 experiments; T lymphocytes plus IL-2—5 experiments], in which 50,000 cells were analyzed per data point. Statistical analysis was performed using the student t-test. In Table 2, a=p<0.05 and b=p<0.02 relative to the respective control.

TABLE 2

| | | % apoptotic cells | |
|---|---|---|---|
| | Treatment | Control | Apo-2L |
| B lymphocytes | none | 40.1 ± 4.1 | 53.2 ± 3.3[a] |
| | LPS | 44.8 ± 2.8 | 55.9 ± 3.2[a] |

TABLE 2-continued

| | | % apoptotic cells | |
|---|---|---|---|
| | Treatment | Control | Apo-2L |
| T lymphocytes | none | 6.3 ± 0.6 | 8.2 ± 0.8 |
| | PMA/ionomycin | 40.3 ± 4.4 | 54.2 ± 3.3[a] |
| | IL-2 pretreatment | 13.7 ± 1.2 | 34.5 ± 4.8[b] |

Apo-2 ligand induced significant apoptosis in unstimulated B cells, in B cells activated by LPS and in T cells activated with PMA and ionomycin. It was previously reported that peripheral T cells can be predisposed to apoptosis by culturing the cells in the presence of IL-2 [Lenardo et al., Nature, 353:858–861 (1991)]. The present study showed that pretreatment with IL-2 did sensitize the peripheral T cells to Apo-2 ligand-induced death.

Example 7

Inhibition Assay Using Fas/Apo-1 and TNF Receptors

An assay was conducted to determine if the Fas/Apo-1 receptor, as well as the type 1 and type 2 TNF receptors (TNF-R1 and TNF-R2), are involved in mediating the apoptotic activity of Apo-2 ligand by testing if soluble forms of these receptors are capable of inhibiting the apoptotic activity of purified, soluble Apo-2 ligand (described in Example 3).

9D cells were incubated ($5 \times 10^4$ cells/well) for 24 hours with a media control or Apo-2 ligand (0.3 μg/ml, prepared as described in Example 3) in the presence of buffer control, CD4-IgG control (25 μg/ml), soluble Apo-1-IgG (25 μg/ml), soluble TNFR1-IgG (25 μg/ml) or soluble TNFR2-IgG fusion protein (25 μg/ml). Soluble derivatives of the Fas/Apo-1, TNF-R1 and TNF-R2 receptors were produced as IgG fusion proteins as described in Ashkenazi et al., Methods, 8:104–115 (1995). CD4-IgG was produced as an IgG fusion protein as described in Byrn et al., Nature, 344: 667–670 (1990) and used as a control.

Figure 3C:
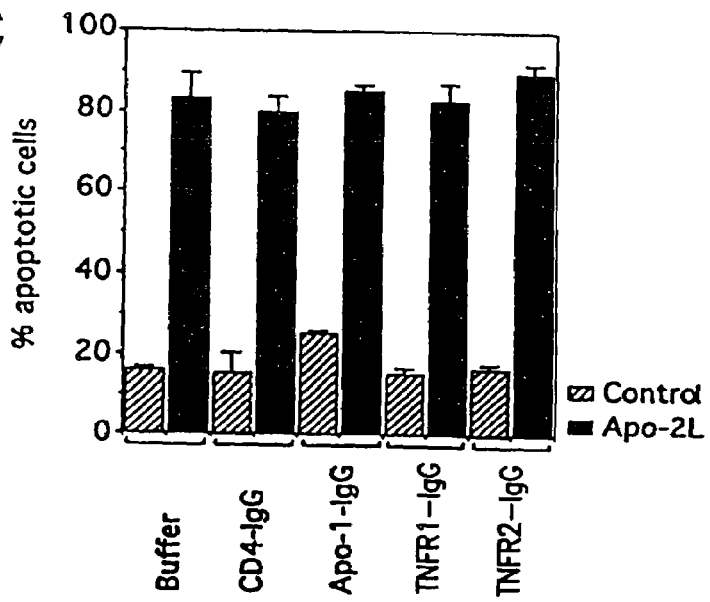

As shown in FIG. 3C, none of the receptor-fusion molecules inhibited Apo-2 ligand apoptotic activity on the 9D cells. These results indicate that Apo-2 ligand apoptotic activity is independent of Fas/Apo-1 and of TNF-R1 and TNF-R2.

Example 8

Expression of Apo-2 Ligand mRNA in Mammalian Tissues

Figure 4:
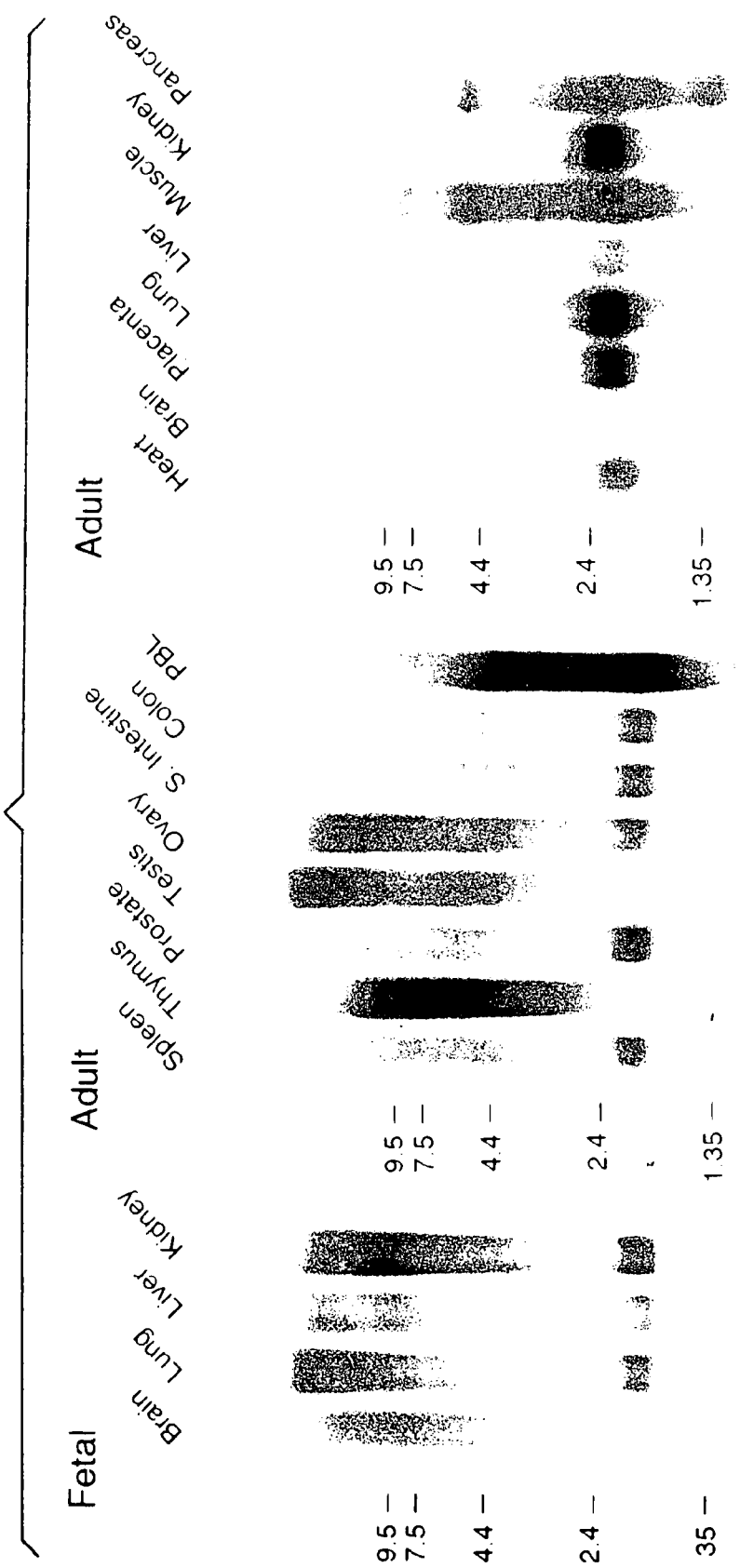
FIG. 4 shows the expression of Apo-2 ligand mRNA in human fetal and human adult tissues, as measured by Northern blot analysis.

Expression of Apo-2 ligand mRNA in human tissues was examined by Northern blot analysis (FIG. 4). Human RNA blots were hybridized to a $^{32}$P-labeled DNA probe based on the full-length Apo-2 ligand cDNA, or to a $^{32}$P-labeled RNA probe based on the GenBank EST sequence, HHEA47M (see Example 1). Human fetal RNA blot MTN (Clontech) and human adult RNA blot MTN-II (Clontech) were incubated with the DNA probe, while human adult RNA blot MTN-I (Clontech) was incubated with the RNA probe. Blots were incubated with the probes in hybridization buffer (5×SSPE; 2× Denhardt's solution; 100 mg/mL denatured sheared salmon sperm DNA; 50% formamide; 2% SDS) for 16 hours at 42° C. The blots were washed several times in 1×SSPE; 2% SDS for 1 hour at 65° C. and 50' freshly deionized formamide; 1×SSPE; 0.2% SDS for 30 minutes at 65° C. The blots were developed after overnight exposure, using a phosphorimager (Fuji).

The results are shown in FIG. 4. In fetal human tissues, Apo-2 ligand mRNA expression was detected in lung, liver and kidney, but not in brain tissue. In adult human tissues, Apo-2 ligand mRNA expression was detected in spleen, thymus, prostate, ovary, small intestine, peripheral blood lymphocytes, heart, placenta, lung, and kidney. Little or no expression was detected in testis, brain, skeletal muscle, and pancreas. The expression profile observed for Apo-2 ligand, as described above, is not identical to that of Apo-1 ligand, which is expressed primarily in T cells and testis [Nagata et al., supra].

Deposit of Material

The following cell line has been deposited with the American Type Culture Collection, 10801 University Boulevard Manassas, Va., USA (ATCC):

| Cell line | ATCC Dep. No. | Deposit Date |
|---|---|---|
| 2935-pRK5-hApo-2L-myc clone 2.1 | CRL-12014 | Jan. 3, 1996 |

This deposit was made under the provisions of the Budapest Treaty on the International Recognition of the Deposit of Microorganisms for the Purpose of Patent Procedure and the Regulations thereunder (Budapest Treaty). This assures maintenance of a viable culture of the deposit for 30 years from the date of deposit. The deposit will be made available by ATCC under the terms of the Budapest Treaty, and subject to an agreement between Genentech, Inc. and ATCC, which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC §122 and the Commissioner's rules pursuant thereto (including 37 CFR §1.14 with particular reference to 886 OG 638).

The assignee of the present application has agreed that if a culture of the cell line on deposit should die or be lost or destroyed when cultivated under suitable conditions, the cell line will be promptly replaced on notification with another of the same plasmid. Availability of the deposited cell line is not to be construed as a license to practice the invention in contravention of the rights granted under the authority of any government in accordance with its patent laws.

The foregoing written specification is considered to be sufficient to enable one skilled in the art to practice the invention. The present invention is not to be limited in scope by the construct deposited, since the deposited embodiment is intended as a single illustration of certain aspects of the invention and any constructs that are functionally equivalent are within the scope of this invention. The deposit of material herein does not constitute an admission that the written description herein contained is inadequate to enable the practice of any aspect of the invention, including the best mode thereof, nor is it to be construed as limiting the scope of the claims to the specific illustrations that it represents. Indeed, various modifications of the invention in addition to those shown and described herein will become apparent to those skilled in the art from the foregoing description and fall within the scope of the appended claims.

What is claimed is:

1. A method of treating a mammal having glioblastoma multiforme, comprising administering to the mammal Apo-2 ligand polypeptide in an amount effective to induce cell death in the mammal's glioblastoma multiforme cells, wherein said Apo-2 ligand polypeptide is selected from the group consisting of:
   (a) a polypeptide comprising amino acid residues 114–281 of FIG. 1A (SEQ ID NO:1):
   (b) a polypeptide consisting of amino acid residues 114–281 of FIG. 1A (SEQ ID NO:1); and
   (c) a polypeptide which is a fragment of (a) or (b).

2. The method of claim 1 wherein said Apo-2 ligand polypeptide consists of amino acid residues 114–281 of FIG. 1A (SEQ ID NO:1).

3. The method of claim 1 wherein said Apo-2 ligand polypeptide is linked to one or more nonproteinaceous polymers selected from the group consisting of polyethylene glycol, polypropylene glycol, and polyoxyalkylene.

4. The method of claim 1 wherein said Apo-2 ligand polypeptide is unglycosylated.

5. A method of treating a mammal having glioblastoma multiforme, comprising administering to the mammal Apo-2 ligand polypeptide in an amount effective to induce cell death in the mammal's glioblastoma multiforme cells, wherein said Apo-2 ligand polypeptide comprises amino acid residues 114–281 of FIG. 1A (SEQ ID NO:1).

6. The method of claim 5 wherein said Apo-2 ligand consists of amino acid residues 114–281 of FIG. 1A (SEQ ID NO:1).

7. The method of claim 5 wherein said Apo-2 ligand polypeptide is linked to one or more nonproteinaceous polymers selected from the group consisting of polyethylene glycol, polypropylene glycol, and polyoxyalkylene.

8. The method of claim 5 wherein said Apo-2 ligand polypeptide is unglycosylated.

\* \* \* \* \*